United States Patent
Wang et al.

(10) Patent No.: US 6,552,803 B1
(45) Date of Patent: *Apr. 22, 2003

(54) DETECTION OF FILM THICKNESS THROUGH INDUCED ACOUSTIC PULSE-ECHOS

(75) Inventors: Haiming Wang, Fremont, CA (US); Shing Lee, Fremont, CA (US); Mehrdad Nikoonahad, Menlo Park, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,664

(22) Filed: Aug. 17, 1999

Related U.S. Application Data

(63) Continuation-in-part of application No. 09/028,417, filed on Feb. 24, 1998, now Pat. No. 6,108,087.

(51) Int. Cl.⁷ .................................... G01B 9/02
(52) U.S. Cl. ....................... 356/503; 356/502
(58) Field of Search ................ 356/502, 503, 356/432

(56) References Cited

U.S. PATENT DOCUMENTS

| | | |
|---|---|---|
| 3,877,813 A | 4/1975 | Hayes et al. |
| 3,978,713 A | 9/1976 | Penney |
| 4,342,517 A | 8/1982 | Johnson et al. |
| 4,379,633 A * | 4/1983 | Bickel et al. ............ 356/359 |
| 4,522,510 A | 6/1985 | Rosencwaig et al. |
| 4,579,463 A | 4/1986 | Rosencwaig et al. |
| 4,619,529 A * | 10/1986 | Iuchi et al. ............ 356/358 |
| 4,627,731 A | 12/1986 | Waters et al. |
| 4,633,715 A | 1/1987 | Monchalin |
| 4,636,088 A | 1/1987 | Rosencwaig et al. |
| 4,679,946 A | 7/1987 | Rosencwaig et al. |
| 4,688,940 A | 8/1987 | Sommargren et al. |
| 4,710,030 A | 12/1987 | Tauc et al. |
| 4,752,140 A | 6/1988 | Cielo et al. |
| 4,865,450 A | 9/1989 | Munechika et al. |
| 4,907,886 A | 3/1990 | Dandliker |

(List continued on next page.)

OTHER PUBLICATIONS

International Search Report mailed Nov. 14, 2000.

"Heterodyne interferometric laser probe to measure continuous ultrasonic displacements," Jean–Pierre Monchalin, *Rev. Sci. Instrum.*, 56(4), Apr. 1985, pp. 543–546.

"Theory of heterodyne pump–probe experiments with femtosecond pulses," A. Mecozzi et al., *J. Opt. Sci. Am. B*, vol. 13, No. 11, Nov. 1996, pp. 2437–2452.

"Low–coherence heterodyne photon correlation spectroscopy," J. Johnson et al., *Applied Optics*, vol. 37, No. 10, Apr. 1, 1998, pp. 1913–1916.

"A New Method of Photothermal Displacement Measurement by Laser Interferometric Probe," S. Sumie et al., *Jpn. J. Appl. Phys.*, vol. 31, Part 1, No. 11, Nov. 11, 1992, pp. 3575–3583.

Primary Examiner—Frank G. Font
Assistant Examiner—Andrew H. Lee
(74) Attorney, Agent, or Firm—Parsons Hsue & deRuntz LLP

(57) ABSTRACT

Thickness of a film in a sample may be detected by directing pump laser pulses to the surface of a sample to generate an acoustic pulse in a sample. The acoustic pulse propagates downwards until it reaches an interface between the bottom of the film and a substrate and is reflected back to the top surface of the film as a first echo. A reflection of the first echo propagates downwards and is again reflected back towards the surface as a second echo. Heterodyne interferometry is used to measure the lapse of time between the first and second echos from which the thickness of the film may be determined.

64 Claims, 19 Drawing Sheets

U.S. PATENT DOCUMENTS

| | | |
|---|---|---|
| 4,921,348 A | 5/1990 | Yeung et al. ............... 356/128 |
| 4,938,596 A | 7/1990 | Gauthier et al. |
| 5,080,491 A | 1/1992 | Monchalin et al. |
| 5,083,869 A | 1/1992 | Nakata et al. |
| 5,294,289 A | 3/1994 | Heinz et al. |
| 5,298,970 A | 3/1994 | Takamatsu et al. |
| 5,377,006 A | 12/1994 | Nakata |
| 5,479,259 A | 12/1995 | Nakata et al. |
| 5,585,921 A | 12/1996 | Pepper et al. |
| 5,604,592 A | 2/1997 | Kotidis et al. |
| 5,619,326 A | 4/1997 | Takamatsu et al. |
| 5,623,307 A | 4/1997 | Kotidis et al. |
| 5,672,830 A | 9/1997 | Rogers et al. |
| 5,677,767 A | 10/1997 | Shirasaki et al. |
| 5,838,485 A | 11/1998 | de Groot et al. |
| 5,926,273 A * | 7/1999 | Kimura et al. ........... 423/242.7 |
| 6,108,087 A * | 8/2000 | Nikoonahad et al. ....... 356/359 |

* cited by examiner

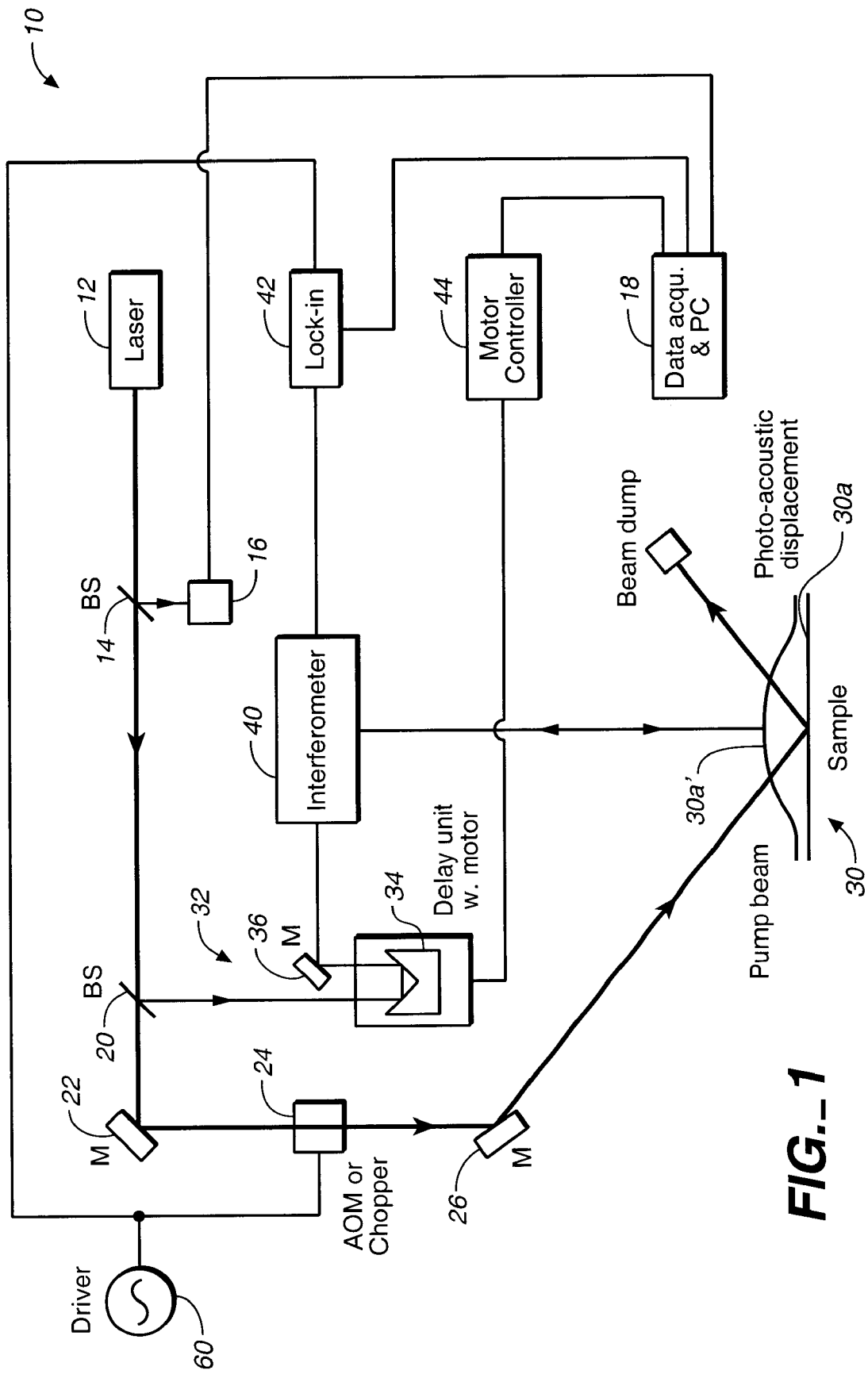
FIG._1

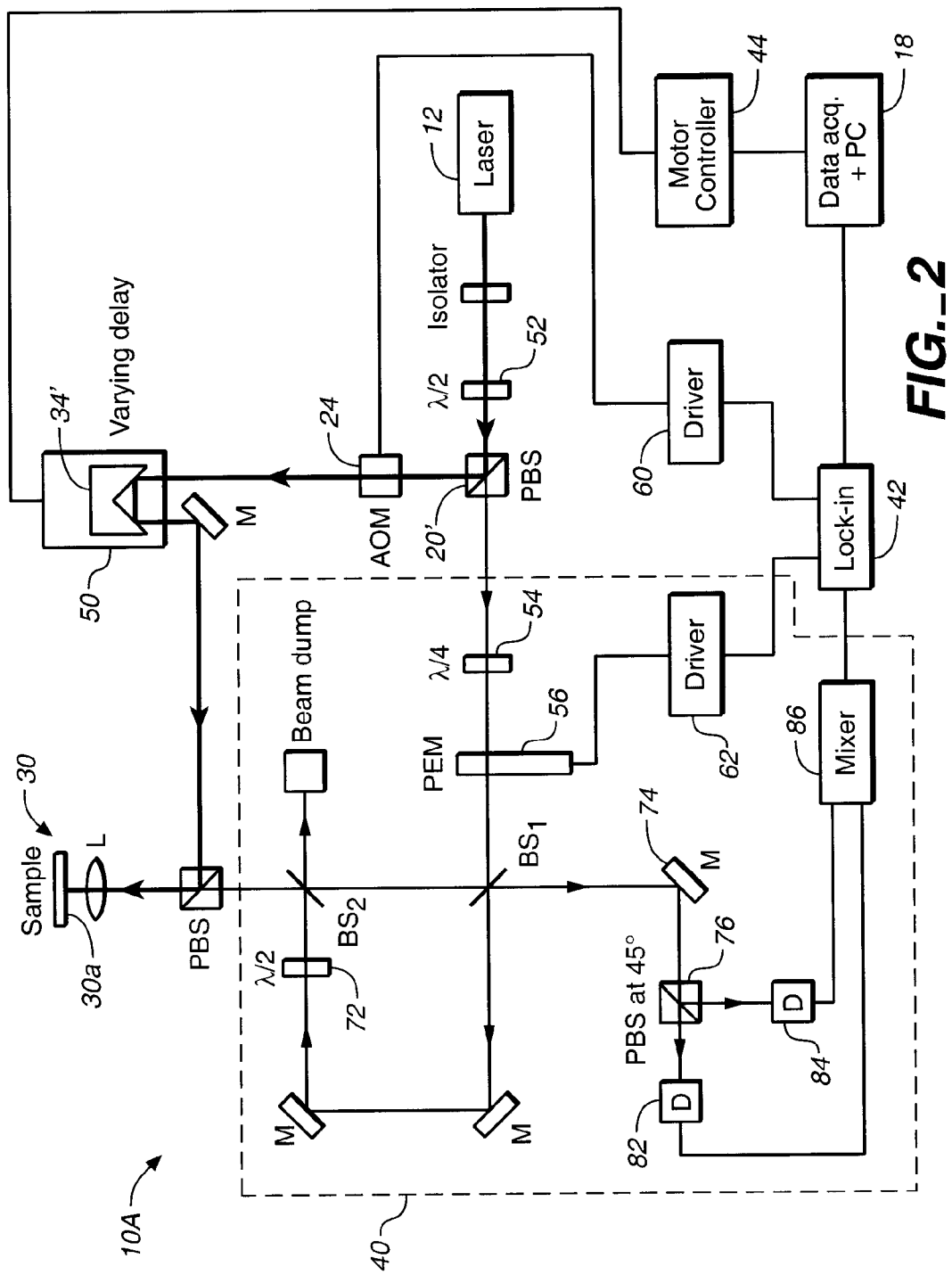
FIG._2

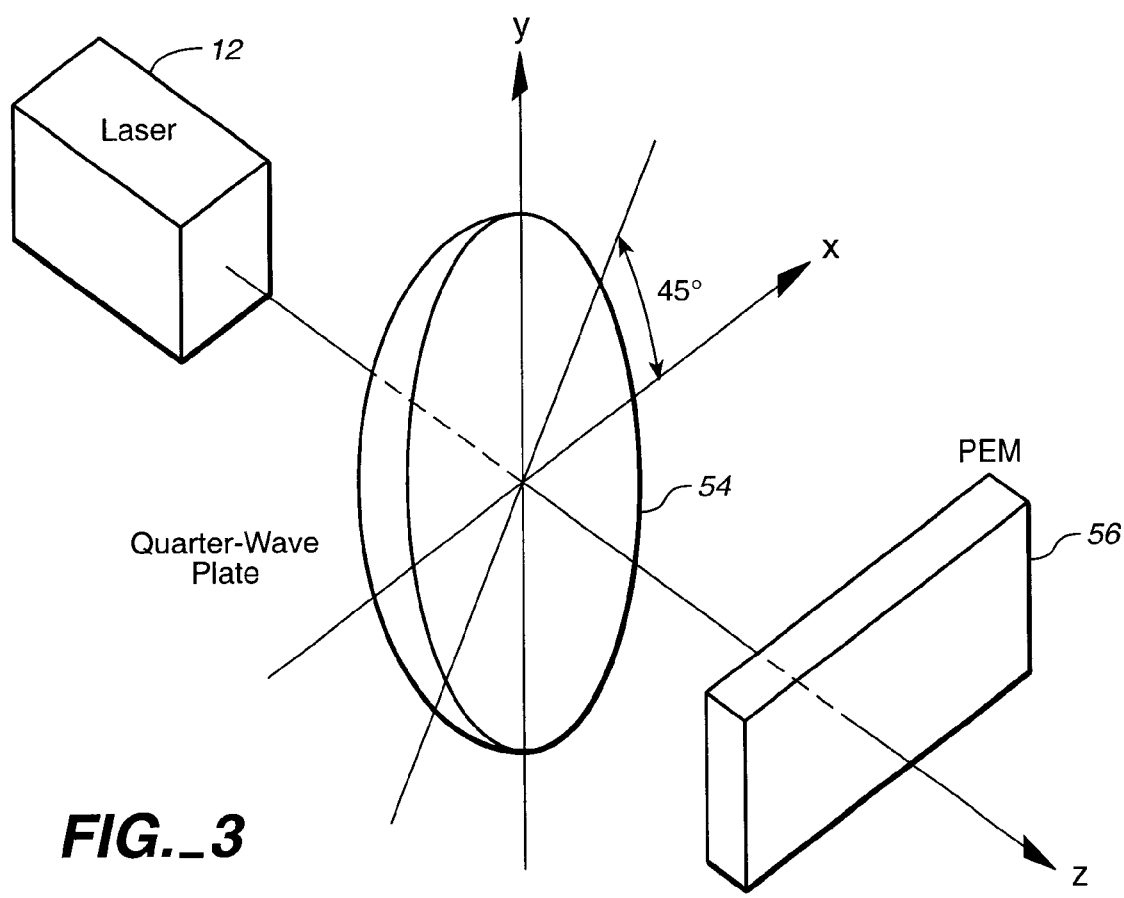
FIG._3

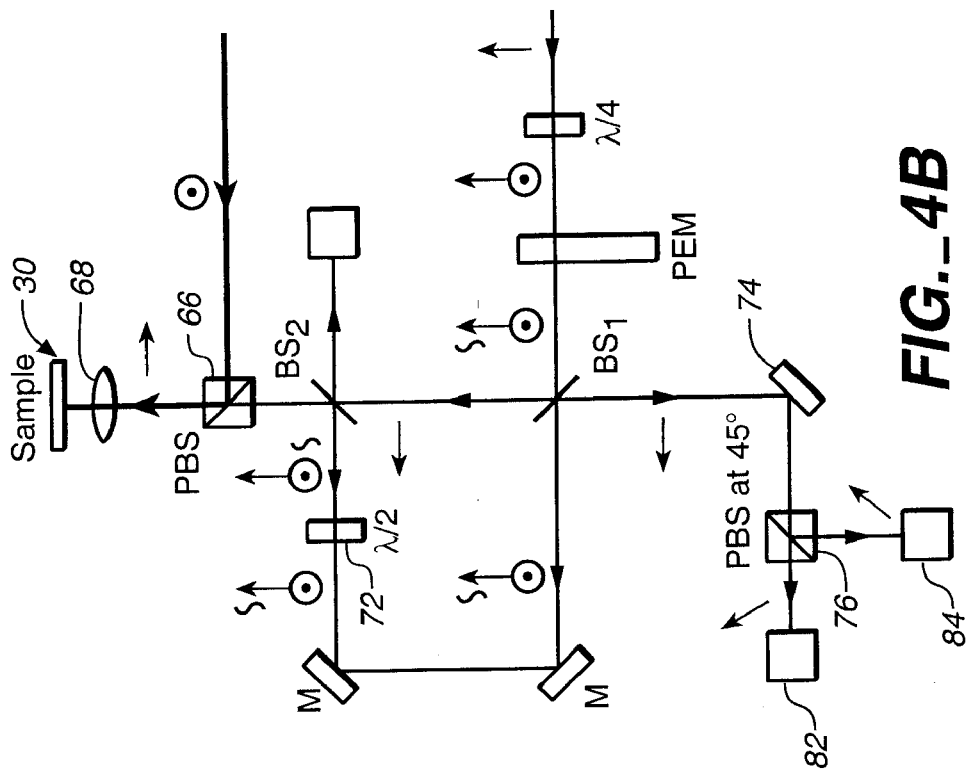
FIG._4B
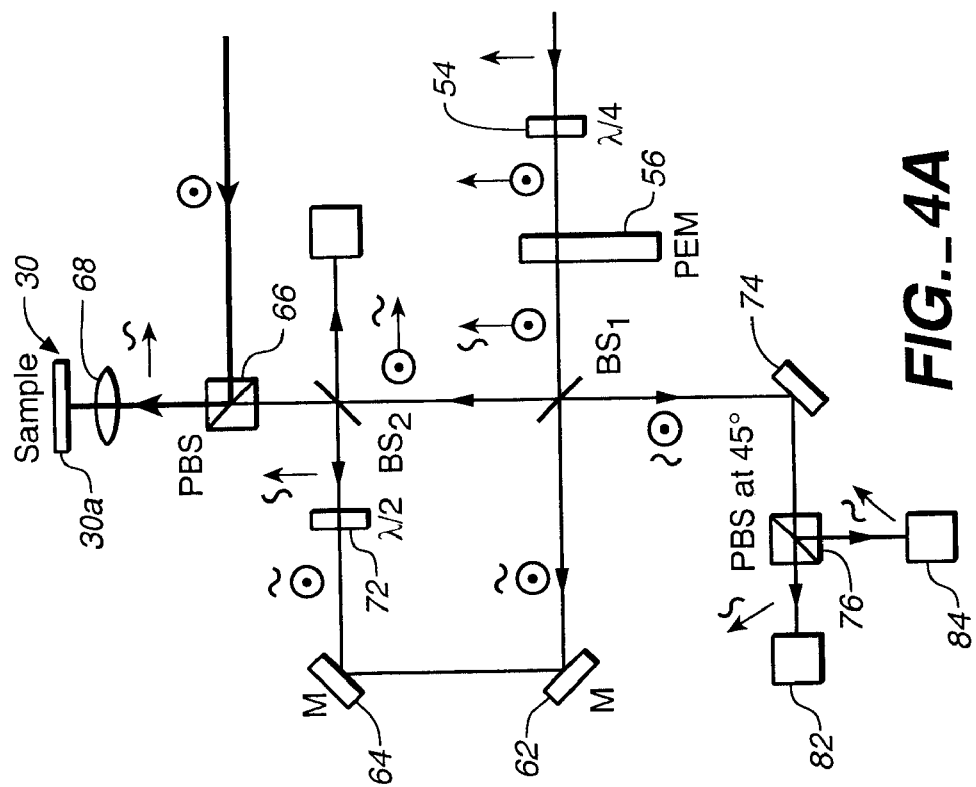
FIG._4A

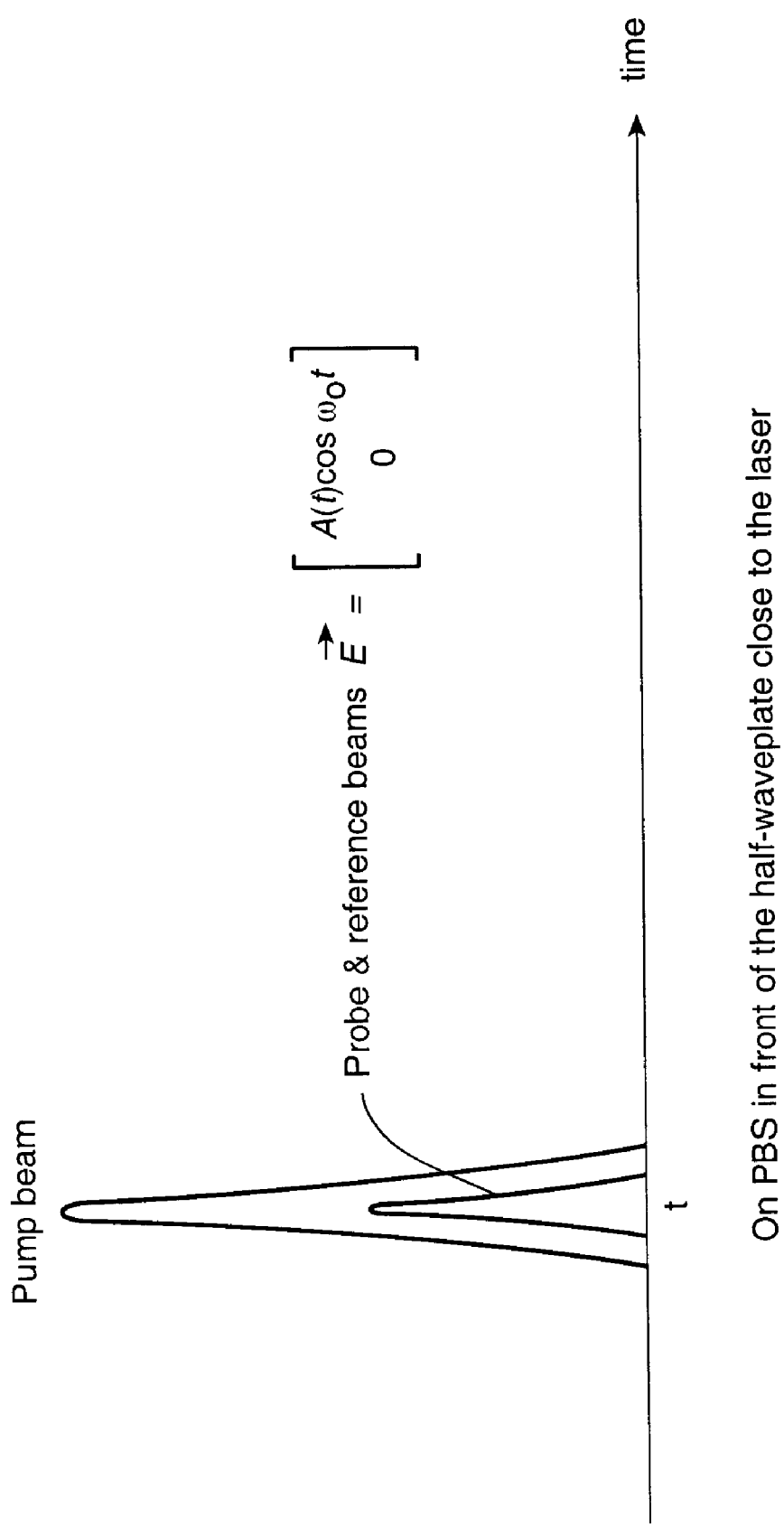
FIG._5A

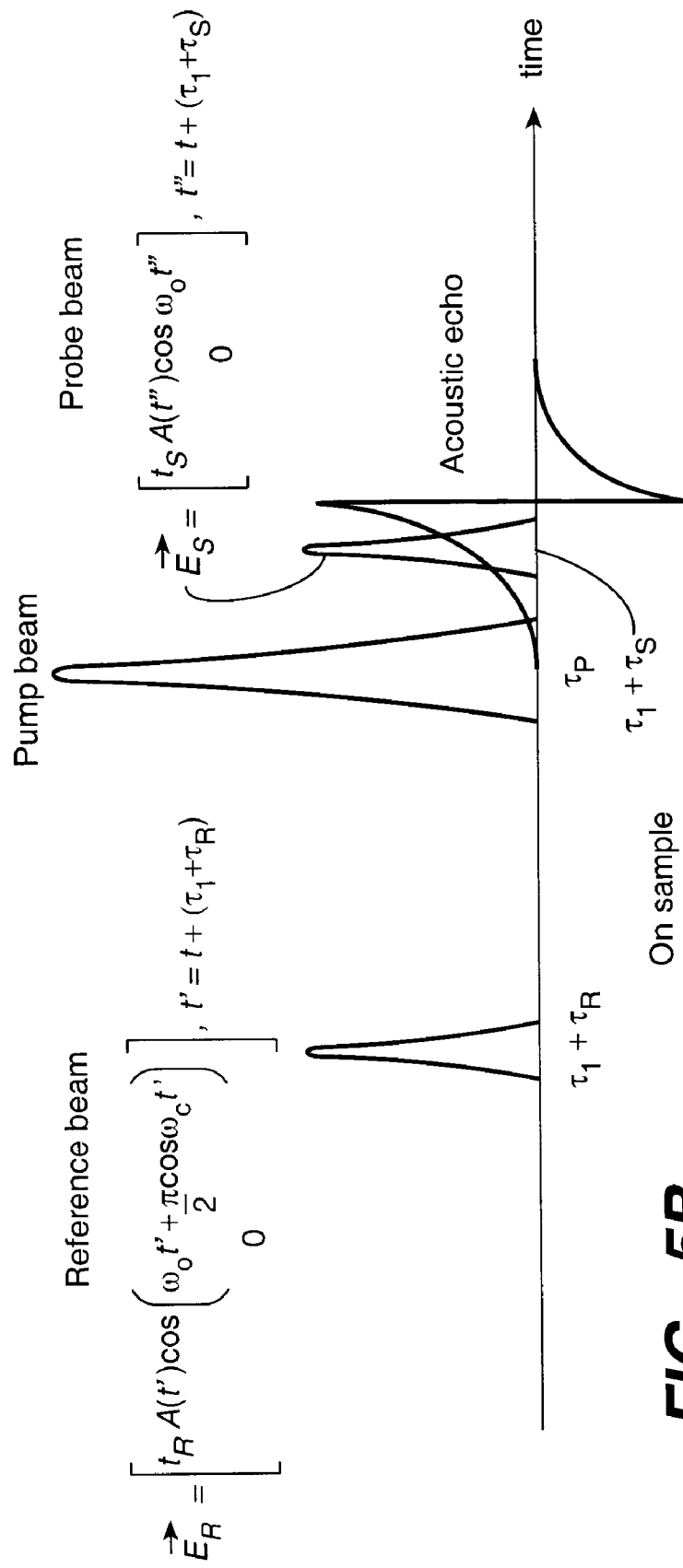
FIG._5B

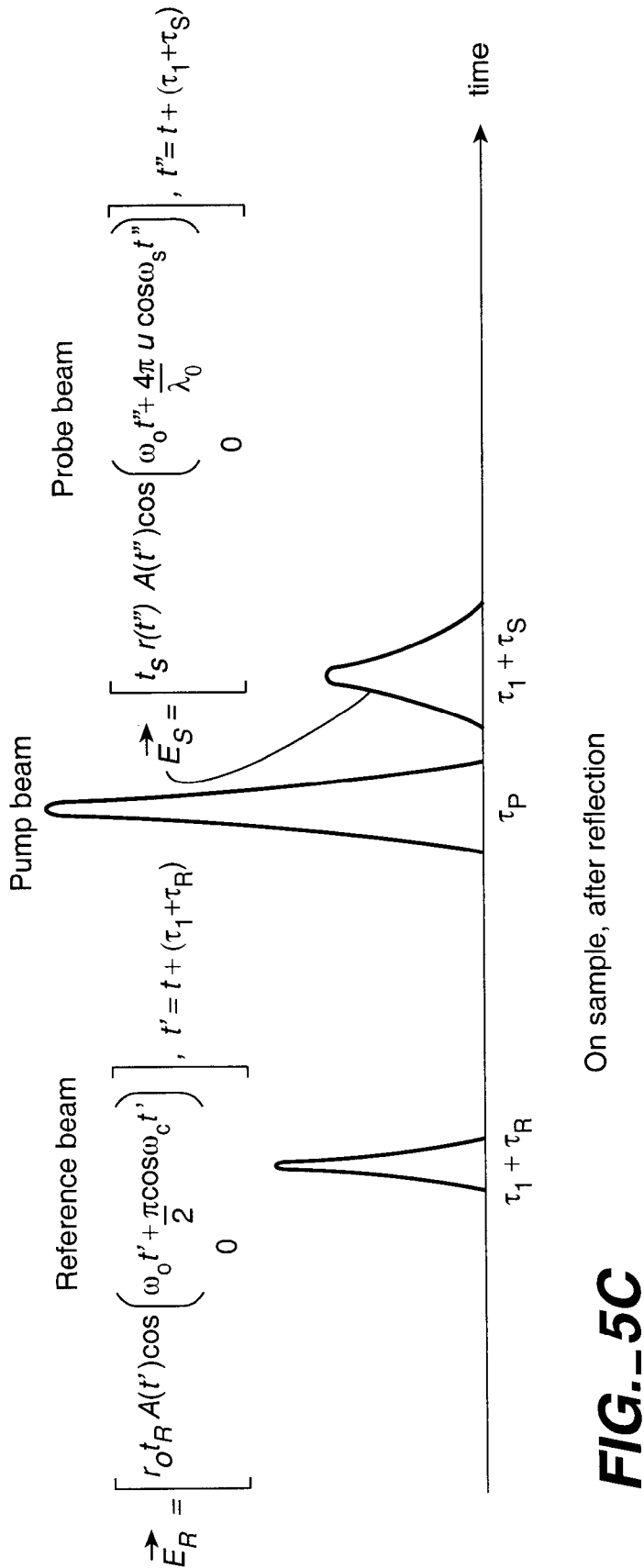
FIG._5C

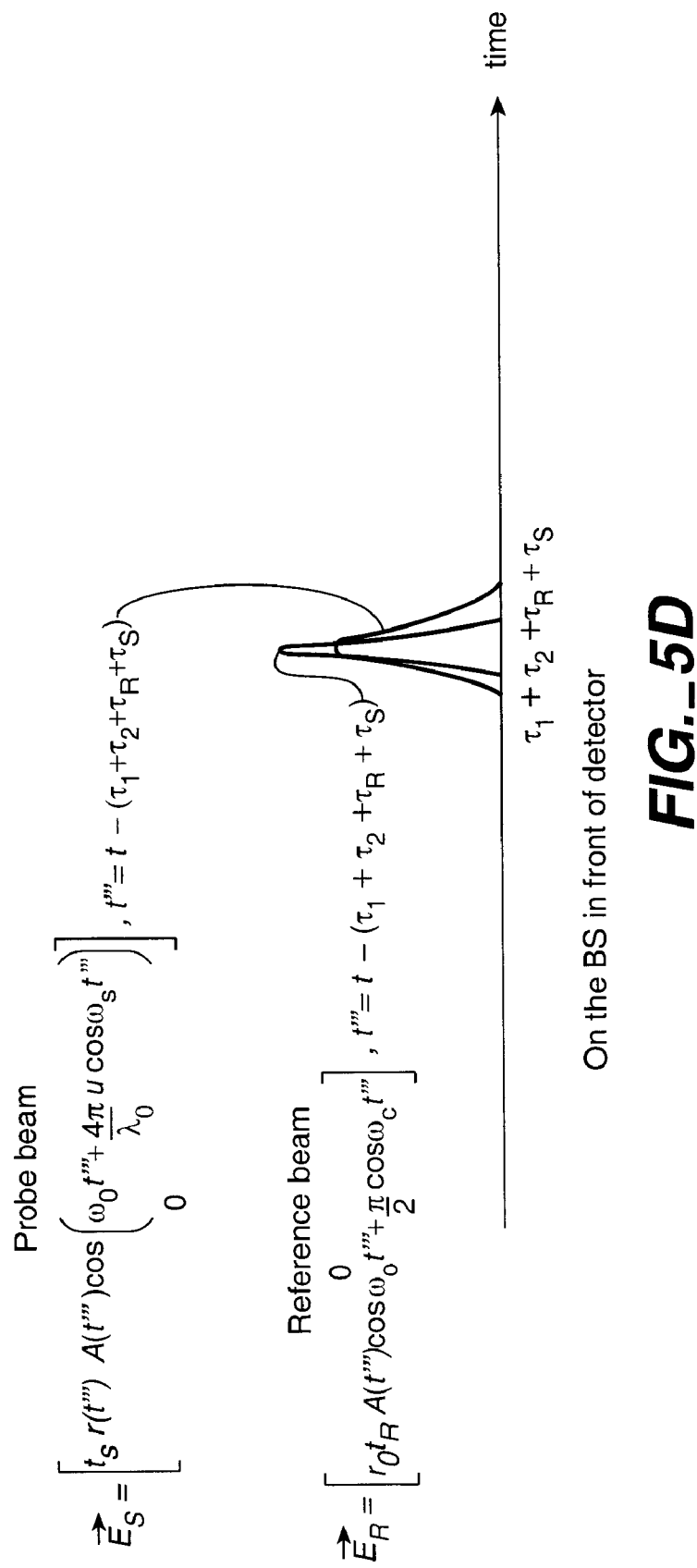
FIG._5D

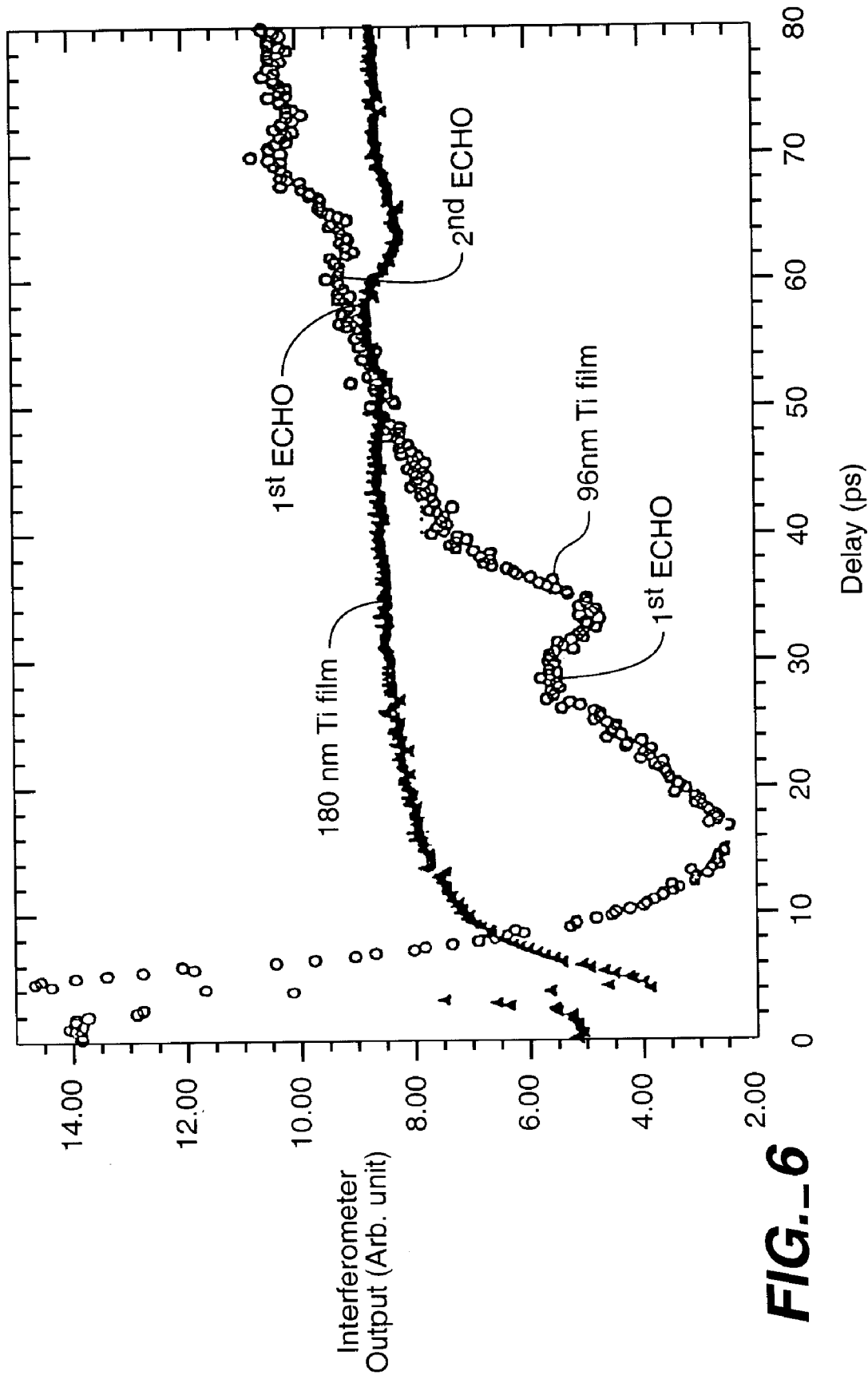
FIG._6

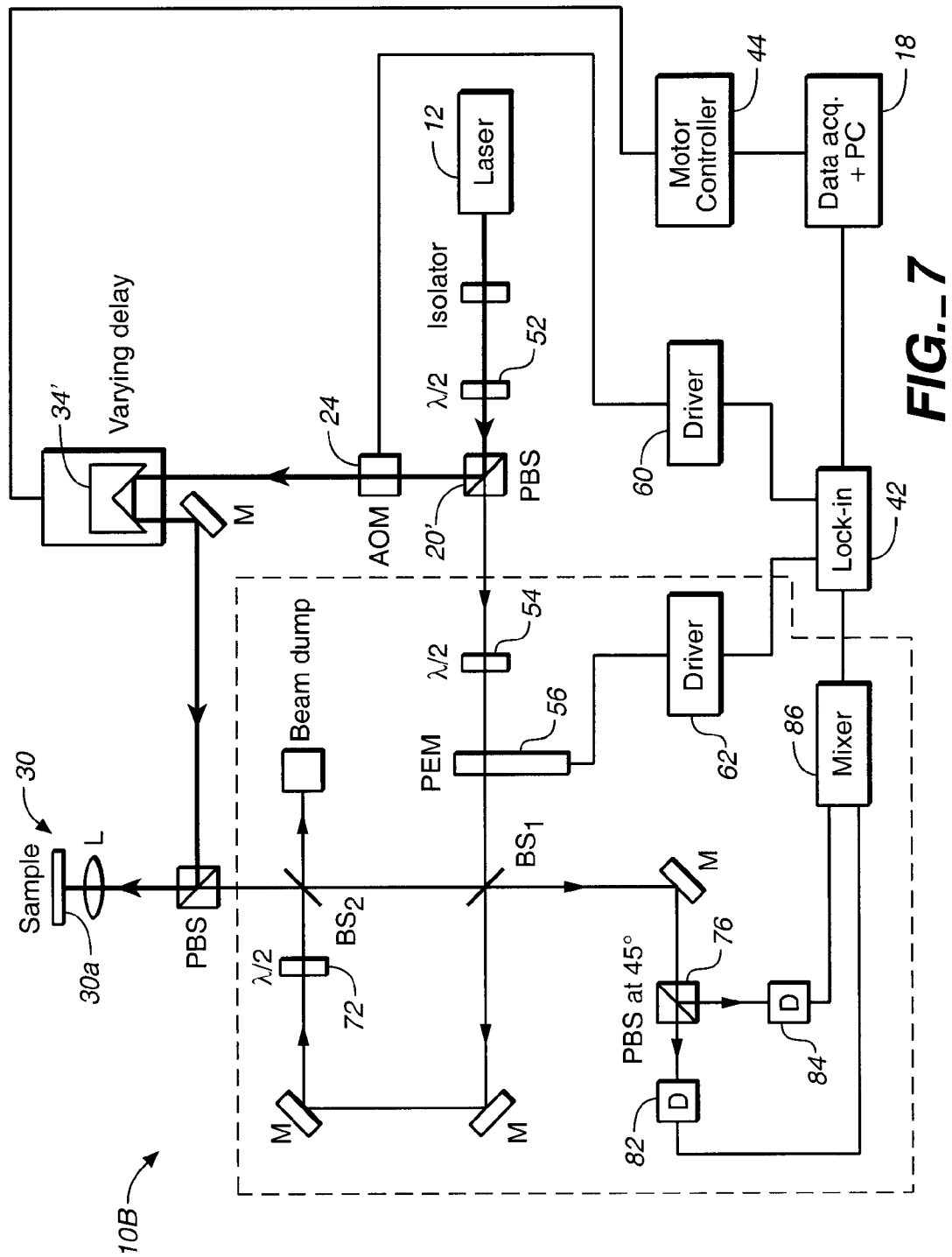

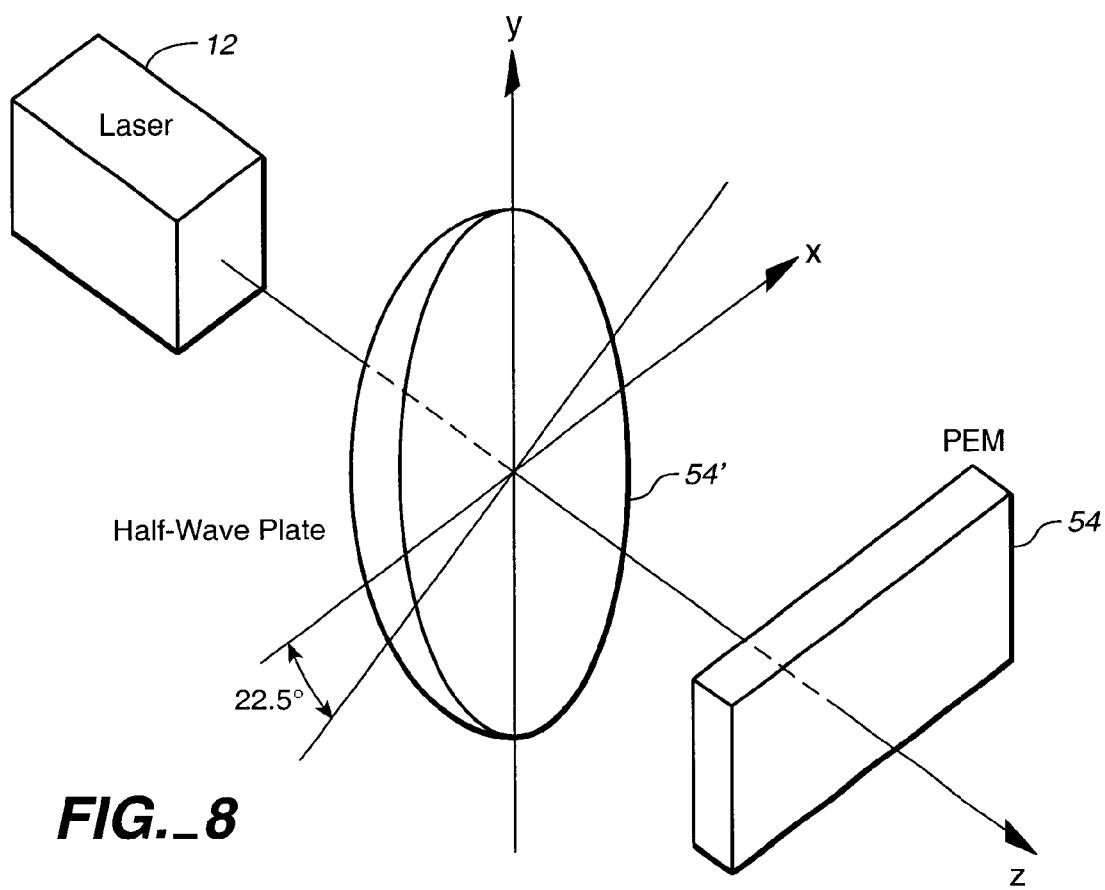
FIG._8

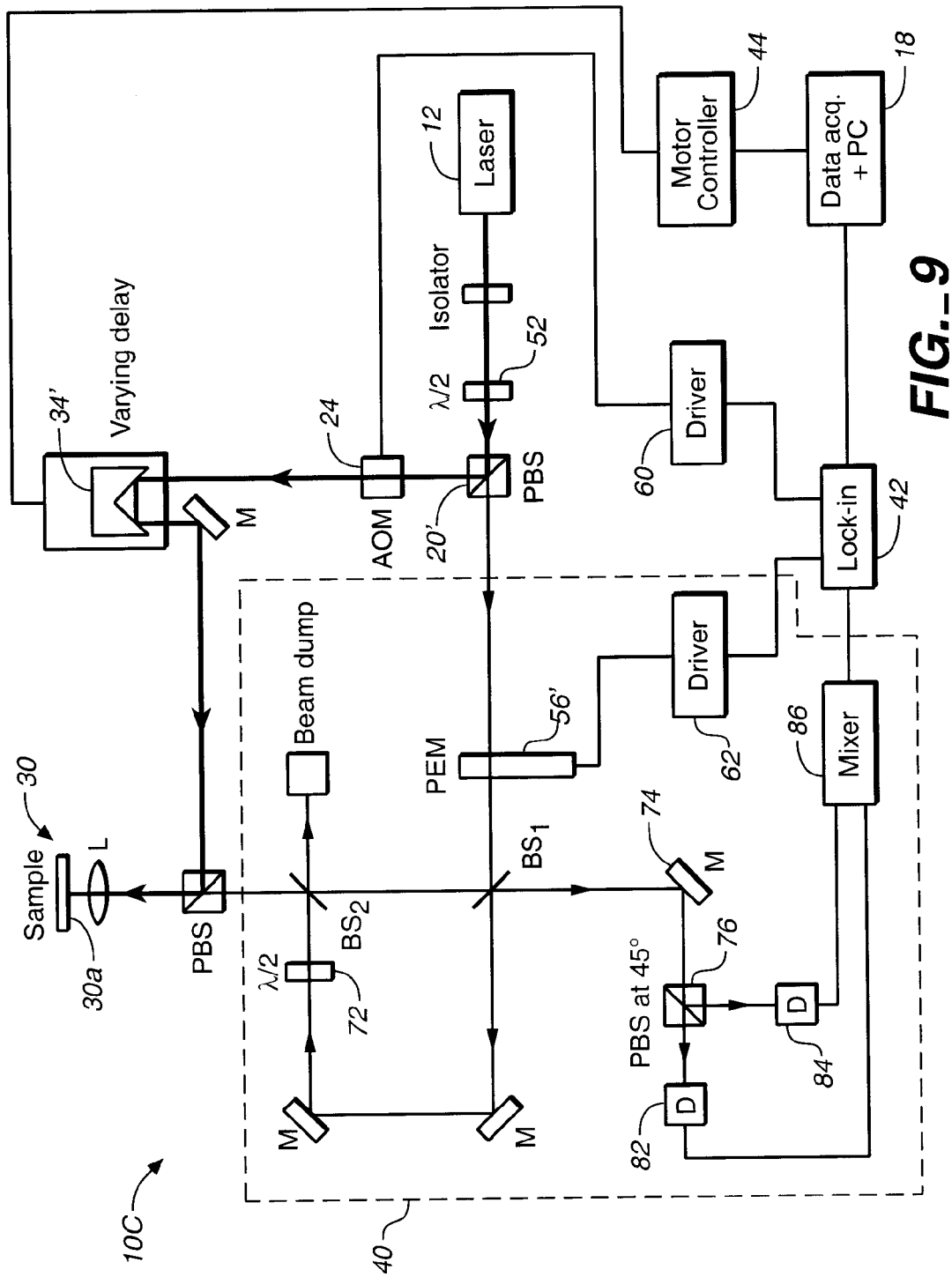
FIG._9

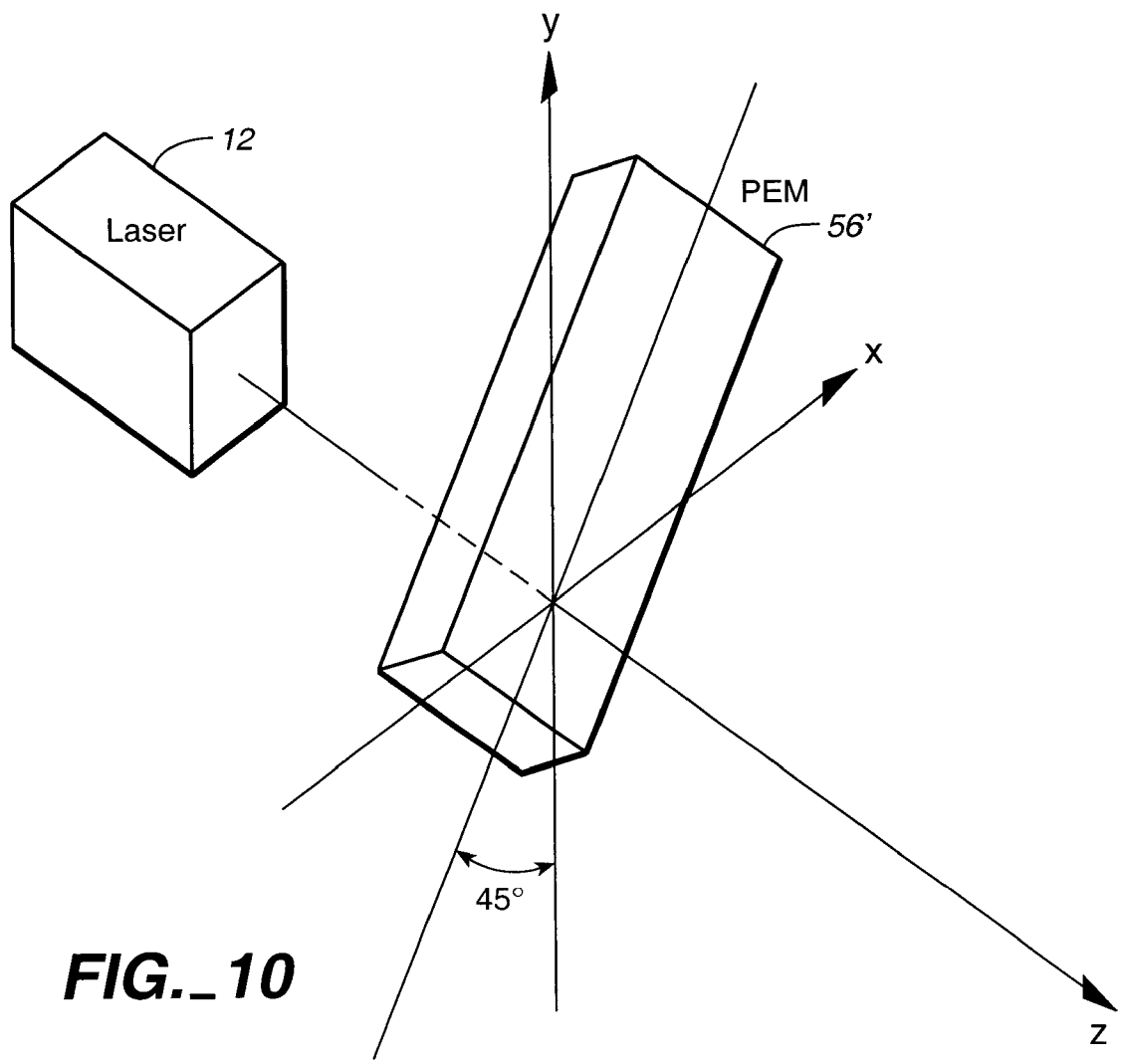
FIG._10

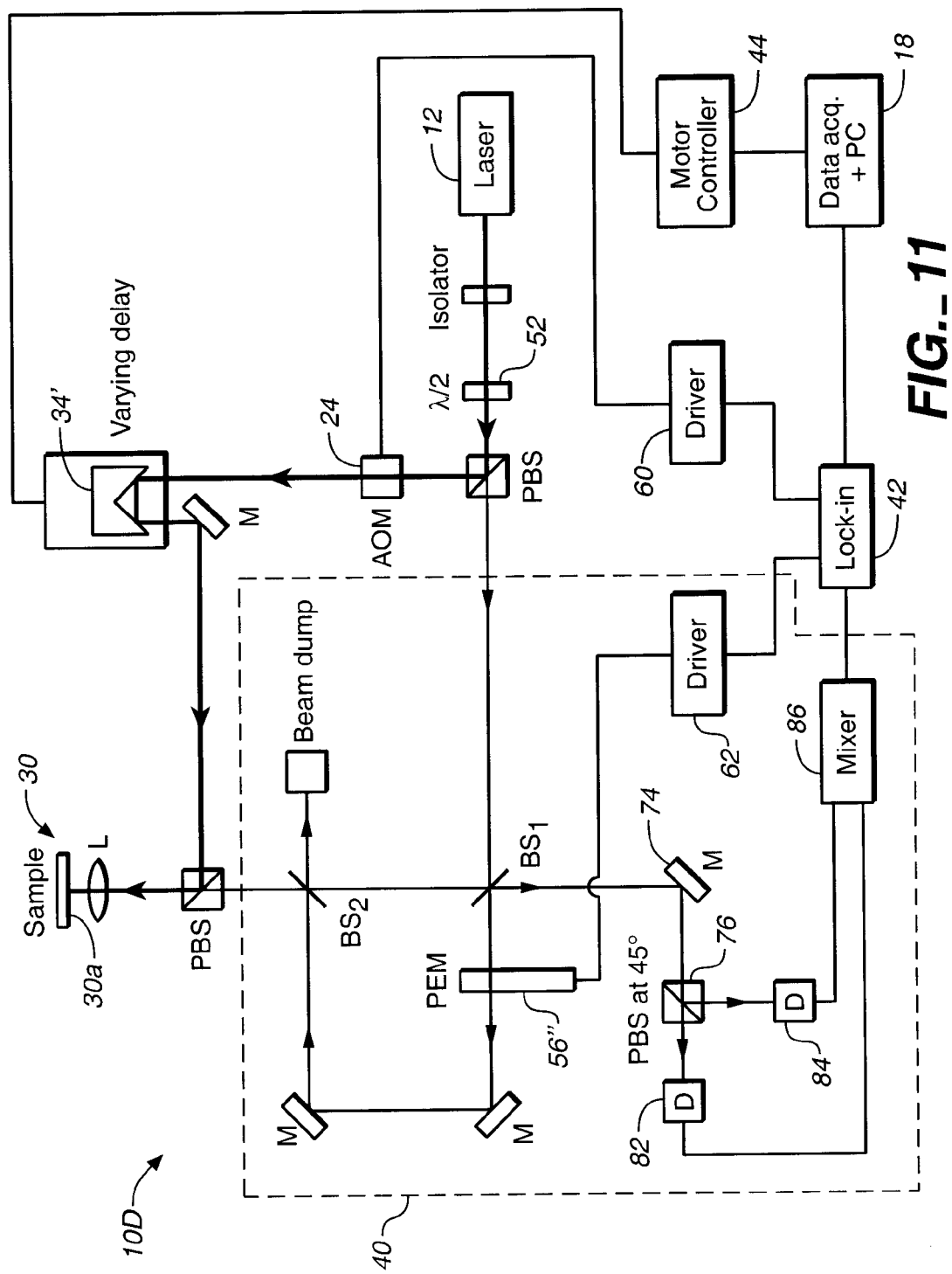
FIG._11

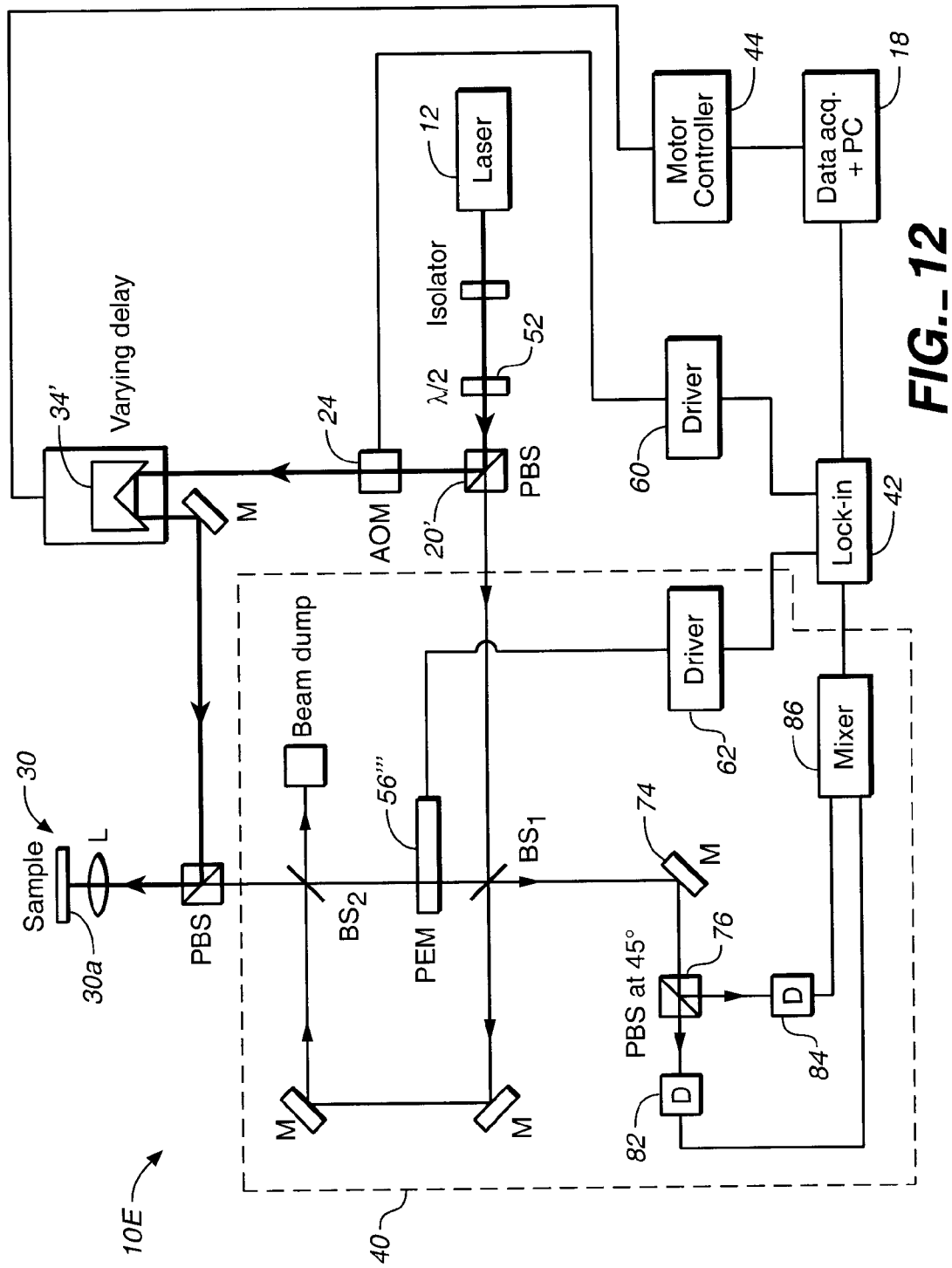
*FIG._12*

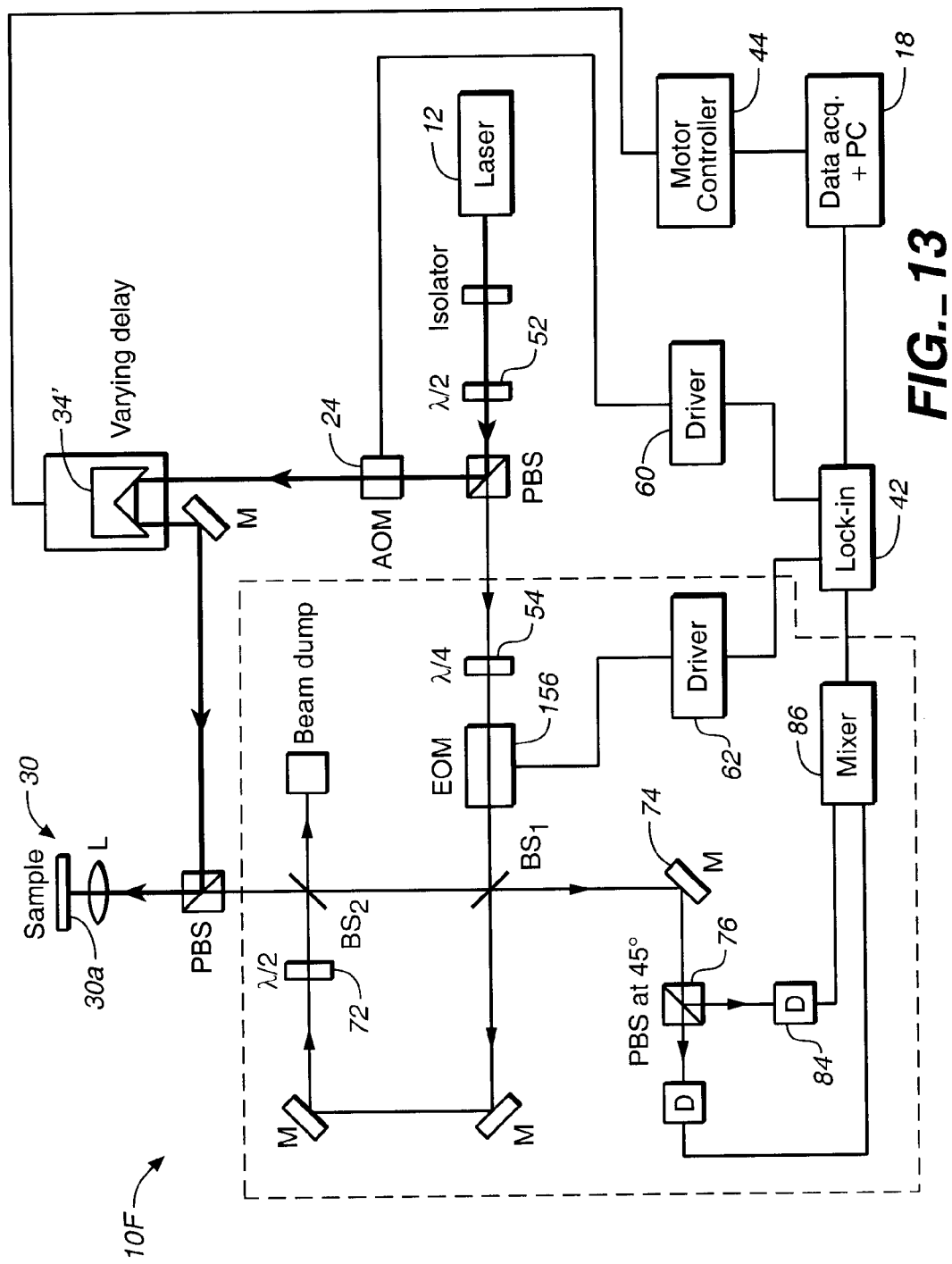
FIG._13

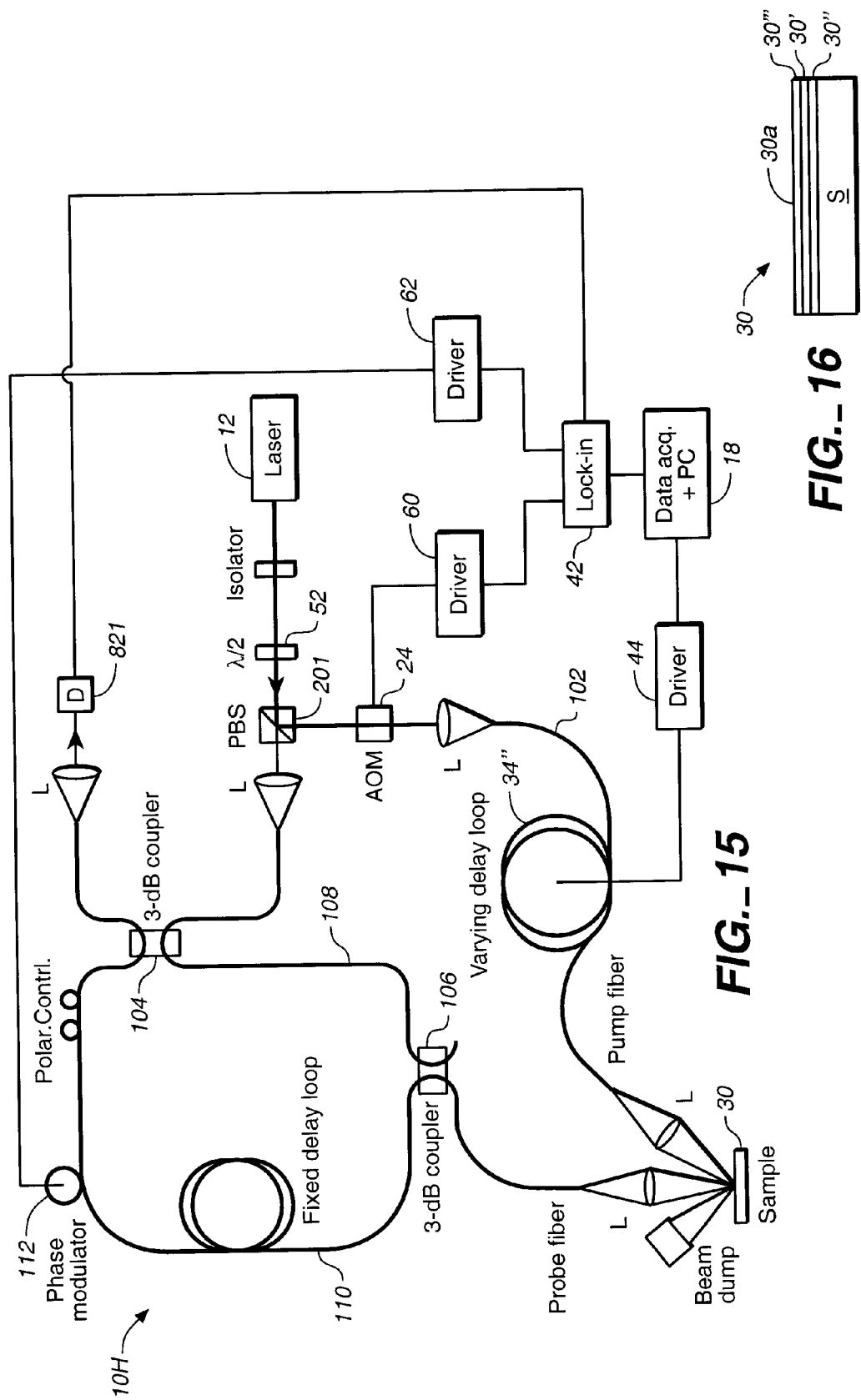
FIG._15
FIG._16

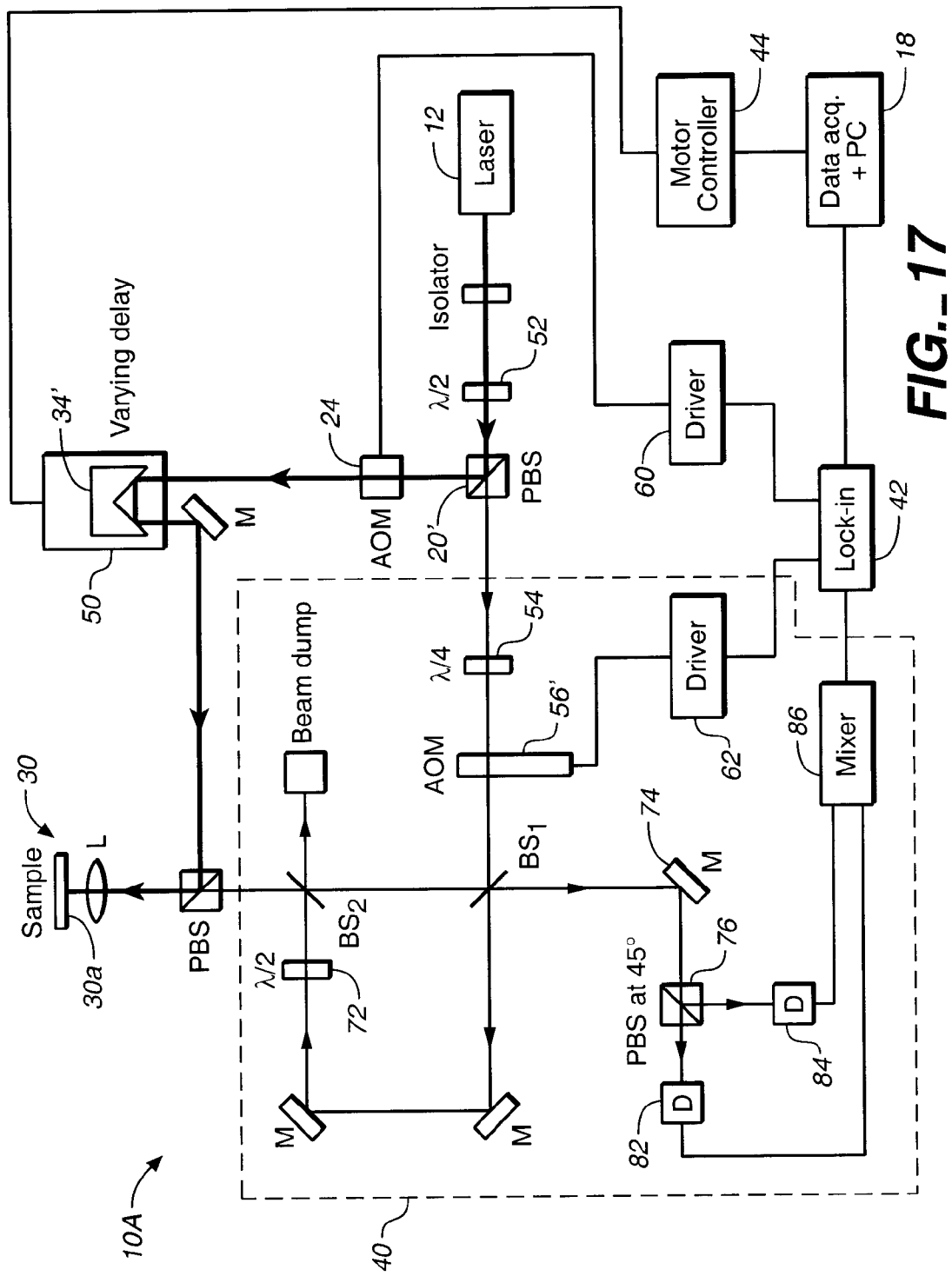
FIG._17

DETECTION OF FILM THICKNESS THROUGH INDUCED ACOUSTIC PULSE-ECHOS

CROSS REFERENCE TO RELATED APPLICATION

This application is a continuation-in-part of U.S. patent application Ser. No. 09/028,417, filed Feb. 24, 1998 now U.S. Pat. No. 6,108,087.

BACKGROUND OF THE INVENTION

This invention relates in general to thickness measurement of structures and, in particular, to a system for measuring film thickness through laser induced acoustic pulse-echo using non-contact interferometry.

Ellipsometry is a powerful technique for film thickness measurement in semiconductor processing. In cases where the film under examination is transparent to the illuminating radiation, ellipsometry can measure films down to one monolayer thick (3–10 Angstroms). However, ellipsometry fails in cases where the film under examination is opaque. Metallic films, which play a major role in integrated circuit fabrication, fall into this category. Optical radiation is absorbed within the first few tens to hundreds of Angstroms of the film, depending on the wavelength and material under examination. For example, using green radiation at a wavelength of 0.5 micron in aluminum, the absorption length is less than 70 Angstroms. At longer wavelengths, and in particular at infra-red wavelengths, this situation gets better, but still ellipsometry cannot provide the full solution with reference to metallic films or other optically opaque films.

Time resolved pulse-echo ultrasound is a well known technique for thickness measurement in situations where the thickness of interest is a few millimeters or at least tens of microns. For films used in semiconductor processing, one needs extremely short pulses so that the surface echo can be time resolved. Such pulses can be generated by short laser pulses and the general area of this art is known as photoacoustics. The physical processes involved is as follows: a short laser pulse is absorbed within one absorption length from the surface, causing a rise in local temperature of the surface. Through the temperature coefficient of expansion (expansivity) the film undergoes thermal stresses leading to an elastic pulse which propagates across the film at the speed of sound. Given the velocity of sound in the film, if one measures the time of flight across the film, one can compute the film thickness. The key-remaining issue, is therefore, the detection of the acoustic disturbance once it bounces back from the rear side of the film and reaches the front surface.

Reference is made to the work of investigators at the Brown University in U.S. Pat. No. 4,710,030. The patent states that once a stress pulse is reflected from the rear side of the film and reaches the surface, it changes the optical constants of the surface and near surface. It can be shown that these changes can be as low as a few parts in $10^6$, depending on both the elastic and electronic properties of the film. The change in the optical constants of the surface leads to a change in reflectivity which is detected by monitoring the intensity in a "probe" beam which also illuminates the surface. Given that the change in optical constants is small, the method patented by workers at Brown University, at best, lacks sensitivity.

The above-described stress pulse not only changes the optical constants of the surface, but also causes a small displacement of the surface. Heterodyne interferometers have been used for detecting movement of surfaces, such as continuous ultrasonic displacements from rough surfaces. See, for example, "Heterodyne Interferometric Laser Probe to Measure Continuous Ultrasonic Displacements," by Monchalin, Rev. Sci. Instrum., Vol. 56, No. 4, April 1985, pp. 543–546. In traditional heterodyne interferometric systems such as that described by Monchalyn, continuous waves (CW) laser sources are used. In the traditional heterodyne interferometer, such as the one described in the Monchalin article, the reference beam and the probe beam travel along different signal paths. Environmental disturbance, such as air turbulence and mechanical vibrations, may introduce different fluctuations in the two paths, causing random noise. Because of such random noise, the signal-to-noise ratio of traditional heterodyne interferometers is insufficient for measuring small phase differences, such as those encountered in semiconductor film thickness measurements. Another example of the traditional heterodyne interferometer is that described in U.S. Pat. No. 4,619,529.

It is, therefore, desirable to provide improved techniques for film thickness measurements.

SUMMARY OF THE INVENTION

As noted above, the key issue in measuring film thickness in semiconductors is the detection of the acoustic echo. Applicants propose instead the provision of a pair of probe pulse and reference pulse radiation that are substantially in phase with each other for measuring the acoustic echo. The probe pulse is directed to a circuit area of the sample when it is influenced by the elastic pulse created by the pump pulse and the reference pulse is directed to the same or a different surface area of the sample so that the pair of pulses are modified by the sample. The modified pulses interfere at the detector. At least one of the pair of pulses is modulated in phase or frequency before or after modification by the sample and prior to detection by the detector. By analyzing the detector output, film thickness information may be derived. Since reference and probe pulses are used for measuring the sample surface, the system proposed by Applicants has the required resolution to detect the acoustic echo caused by the elastic wave.

In the preferred embodiment, an optical delay may be used to alter a time relationship between the pump pulse and the probe pulse so that the probe pulse is directed to the sample surface when it is influenced by the elastic pulse created by the pump pulse.

Where the reference and probe signals in the interferometer do not travel along the same path, random noise created by environmental factors may render the interferometer impractical for measuring small phase changes caused by the acoustic echo at the sample surface. Therefore, preferably, the reference and probe pulses are directed along substantially a common optical path between an optical source and the detector.

Where measurement of very thin films or layers is desired, the probe and reference pulses used may have durations of less than about 10 picoseconds. Such scheme is applicable in both heterodyne and homodyne systems, so that one, or both or none of the two pulses is modulated in intensity or phase or frequency.

BRIEF DESCRIPTION OF THE DRAWINGS

FIG. 1 is a schematic diagram of a system for generating elastic pulse(s) in a sample in an interferometer for detecting the elastic pulse(s) for determining film thickness to illustrate the invention.

FIG. 2 is a schematic diagram of a first embodiment of the system of FIG. 1 in a common path configuration.

FIG. 3 is a perspective view of a portion of the system of FIG. 1 illustrating the orientation of a photo-elastic modulator relative to the axis of a quarter-wave plate and of the polarization from a laser to illustrate the embodiment of FIG. 2.

FIGS. 4A and 4B are schematic diagrams of a portion of the embodiment of FIG. 2 illustrating the polarization states of, respectively, the reference pulse and the probe pulse in such portion.

FIG. 5A is a timing diagram of the pump pulse and a pulse from which a pair of probe and reference pulses is later derived, when they emerge from the polarizing beamsplitter 20 or 20' in FIGS. 1 or 2.

FIG. 5B is a timing diagram of the pump pulse and a pair of reference and probe pulses when these pulses reach the sample but before they are modified by the sample.

FIG. 5C is a timing diagram of the pump pulse and a pair of reference and probe pulses at the sample after reflection by the sample.

FIG. 5D is a timing diagram of the pair of reflected reference and probe pulses upon reaching the polarizing beam splitter in front of the detector of FIG. 2.

FIG. 6 is a plot of measured signal output as a function of time of the detector of FIG. 2 in measuring a metal layer of two different thicknesses to illustrate the invention.

FIG. 7 is a schematic diagram of a second embodiment of the system of FIG. 1.

FIG. 8 is a perspective view of a photo-elastic modulator, half-wave plate and laser illustrating the orientation of the modulator relative to the axis of the half-wave plate and of the polarization plane of the radiation from the laser to illustrate the embodiment of FIG. 7.

FIG. 9 is a schematic diagram of a third embodiment of the system of FIG. 1.

FIG. 10 is a perspective view of the photo-elastic modulator and laser of FIG. 9 illustrating the relative orientation of the modulator and polarization plane of radiation provided by the laser in FIG. 9.

FIGS. 11–14 are schematic diagrams for four additional embodiments of the system of FIG. 1.

FIG. 15 is a schematic diagram of an additional embodiment of the system of FIG. 1, where at least some of the optical paths are implemented using optical fibers.

FIG. 16 is a cross-sectional view of a sample comprising a layer of metal among other layers over a substrate to illustrate the invention.

FIG. 17 is a schematic diagram of a system for generating elastic pulse(s) in the sample in an interferometer for detecting the elastic pulse(s) for determining film thickness to illustrate yet another embodiment of the invention.

For simplicity in description, identical components are labeled by the same numerals in this application.

DETAILED DESCRIPTION OF THE PREFERRED EMBODIMENT

Figure 14:
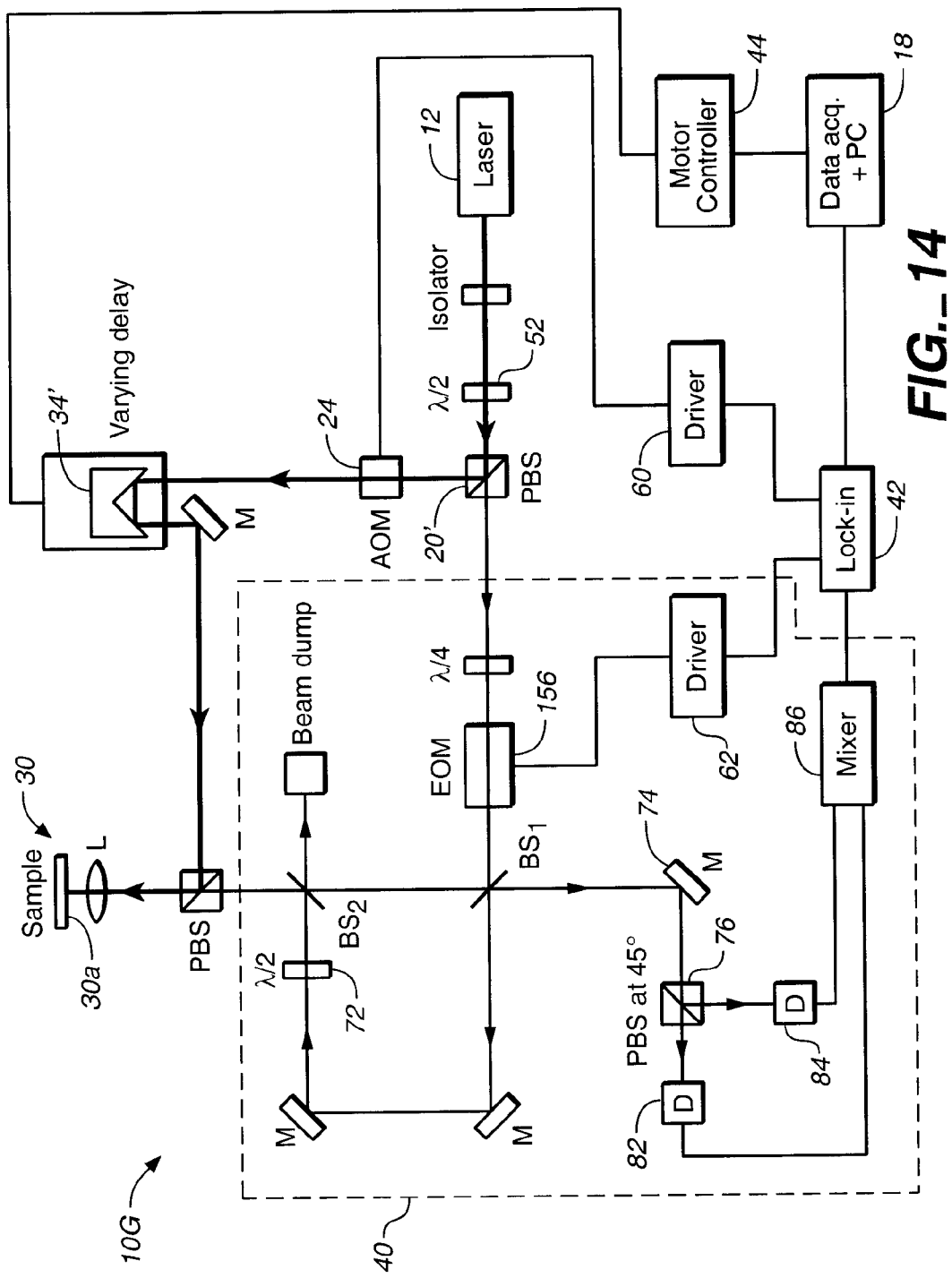

FIG. 1 is a schematic diagram of a system 10 for inducing one or more elastic pulse(s) in a sample, where system 10 includes an interferometer for detecting the elastic pulse(s) to determine the film thickness of the sample and to illustrate a preferred embodiment. As shown in FIG. 1, system 10 includes a laser 12 supplying radiation at an optical frequency, in the form of a beam of periodic sequence of pulses at a first frequency to beamsplitter 14 which diverts a portion of the beam towards a detector 16. Detector 16 detects variations in intensity of the pulses supplied by laser 12 and supplies such information to data acquisition unit and personal computer 18 for comparison with other data so that errors in the data caused by the intensity fluctuations of the laser 12 may be reduced or eliminated. The bulk of the energy supplied by laser 12 passes through beamsplitter 14 and continues to beamsplitter 20 which divides the energy into two portions: a first portion as pump pulses in a pump beam for generating elastic pulses in the sample and a second portion for use in the interferometer 40 to detect the elastic pulse(s) for film thickness measurement of the sample. To simplify the figures, the detector 16 and beam splitter 14 are omitted in figures subsequent to FIG. 1.

Beamsplitter 20 splits the sequence of pulses from laser 12 into two sequences of the same first frequency; one being the sequence of pump pulses and the other the sequence of pulses that are converted into a sequence of pairs of reference and probe pulses in a manner described below. The sequence of pump pulses are modulated by an acousto-optic modulator (AOM) or chopper 24 which blocks periodically the passage of the sequence of pump pulses at a modulation frequency, so as to generate a periodic burst of pump pulses at a second frequency equal to the frequency at which the pump pulses are let through the AOM or chopper 24.

Thus, as shown in FIG. 1, the pump pulses are reflected by mirror 22 through an AOM or chopper 24 as a sequence of bursts of pulses and reflected by another mirror 26 towards the sample 30. The pulses are supplied by laser 12 at a first frequency of about 100 MHz. Each pump pulse is absorbed within one absorption length from surface 30a of the sample, giving rise to change in local temperature of the surface and causing the surface to undergo thermal stresses leading to an elastic pulse which propagates down through the sample at the speed of sound in the sample. The elastic pulse is reflected by an interface in the sample between different layers as echoes and such echoes propagate back towards the surface 30a of the sample. The elastic pulse and its echoes cause the surface to move to, for example, new positions 30a' for a short time and may also cause optical characteristics of the surface 30a to change.

The second portion of the energy supplied by laser 12 is reflected by beamsplitter 20 along a delay path 32 which comprises a retroreflector 34 mounted on a motorized translation stage and mirror 36 to an interferometer 40 which detects the movement of the surface 30a caused by the elastic pulses. The output of the interferometer 40 is provided to a synchronizing means such as a lock-in amplifier 42 which also receives the modulation second frequency from the AOM or chopper 24. Lock-in amplifier 42 amplifies the output of the interferometer at the modulating frequency of AOM or chopper 24 (or a frequency related to such modulating frequency, as described below) and supplies the amplified signal to data acquisition and personal computer unit 18. Delay unit with motor 36 is controlled by motor controller 44 so as to vary a timing relationship between the pulses supplied by interferometer 40 for sampling surface 30a relative to the pump pulses in a manner described in detail below. Data acquisition and personal computer unit 18 is then used to compute film thickness values. While in FIG. 1, the pump beam is shown to be at an oblique angle to surface 30a, it will be understood that this may or may not be the case, depending on the embodiment of system 10, as described in more detail below.

FIG. 2 is a schematic view of one embodiment 10A of the system of FIG. 1 in a common path/time differential configuration. System 10A differs from system 10 of FIG. 1 in that the beam passed by polarizing beamsplitter 20' is used in the interferometer whereas the beam reflected by the polarizing beamsplitter 20' is the pump beam, and in that the varying delay 34' mounted on a motorized translation stage is in the optical path of the pump beam rather than in the path of the beam to the interferometer 40. The laser beam from laser 12, after passing the half-wave plate 52, is linearly polarized. It is then divided into a pump beam and another beam by the polarizing beamsplitter 20'. As described above, the pump beam is modulated by means of an acousto-optic modulator or chopper 24 at a second modulation frequency as controlled by driver 60. The polarizing beamsplitter 20' reflects a portion of the laser beam towards modulator or chopper 24 to become the pump beam and passes another beam from which the pair of reference and probe pulses are derived. The beam that is passed by splitter 20' is passed through a quarter-wave plate 54 having an axis at an angle (preferably 45°) with respect to a plane (plane of the paper) containing the optical paths of the pump beam, the laser beam from laser 12 and the beam emerging from splitter 20' from which the pair of reference and probe pulses is derived. As a convenient convention in description, such plane or the plane of the paper may be a plane parallel to an optical table and is referred to herein as the horizontal plane, it being understood that this is used for convenience for description only and that the embodiment of FIG. 2 is not limited thereby. In the description that follows, such horizontal direction is indicated by an arrow and a direction perpendicular to such plane is referred to as the vertical direction and indicated by a circle with a center dot. The hat or "S" sign added to one of the above two directions as shown in FIGS. 4A, 4B means that one of the polarization components is phase modulated by a photo-elastic modulator, such as modulator 56 of FIG. 2.

FIG. 3 is a perspective view of laser 12, quarter-wave plate 54 and modulator 56 of FIG. 2 illustrating the relative orientation of the axis of modulator 56 relative to the axis of plate 54 and the polarization plane of radiation supplied by laser 12. In reference to FIG. 3, the XZ plane is the horizontal plane and the Y axis indicates the vertical direction. Thus, in reference to FIG. 3, quarter-wave plate 54 is oriented so that its axis is preferably 45° to the horizontal plane. Therefore, when the radiation from laser 12 passes plate 54, the emerging radiation is circularly polarized. The photo-elastic modulator 56 is oriented so that it will modulate the electric field of the radiation only in either the horizontal plane or along the vertical direction but not both.

For the purpose of illustration, it is assumed that modulator 56 only modulates the component of radiation in the horizontal plane and not that in the vertical direction. The paths of the reference and probe pulses will now be described in reference to FIGS. 2, 4A and 4B.

The laser beam pulse that passes from modulator 56 to beamsplitter $BS_1$ is split into two pulses: a probe pulse and a reference pulse. The reference and probe pulses travel from beamsplitter $BS_1$ to beamsplitter $BS_2$ along two different paths: a short path directly between the two beamsplitters and a long path where signals are reflected by mirrors 62 and 64.

In reference to FIG. 4A, the radiation pulse emerging from photo-elastic modulator 56 and approaching beamsplitter $BS_1$ has a horizontal component which is modulated in phase or frequency by modulator 56 and a vertical component which is not modulated by modulator 56. Beamsplitter $BS_1$ reflects a portion of each of the two components in the beam from modulator 56 as a reference pulse and transmits the remainder (also comprising a portion of each modulated horizontal component and unmodulated vertical component) as a corresponding probe pulse, so that two sequences: a sequence of reference pulses and a sequence of probe pulses will emerge from beamsplitter $BS_1$.

FIG. 4A illustrates the polarization state of the reference pulses and their reflections by the sample. In reference to FIG. 4A, the circularly polarized reference pulses proceed directly from $BS_1$ to $BS_2$ along the short path there between and pass through beamsplitter $BS_2$ to polarizing beamsplitter 66 which passes only the horizontal components of the pulses modulated by modulator 56 through lens 68 to surface 38 of the sample 30. In reference to FIG. 2, the varying delay 34' mounted on the motorized translation stage 50 is adjusted so that the horizontally polarized reference pulse reaches sample 30 before a corresponding pump pulse. Hence, when the horizontally polarized reference pulse reaches the sample, the surface 30a of the sample is stationary and unaffected by the corresponding pump pulse. The pump pulse corresponding to such reference pulse then reaches sample 30 to create an elastic pulse in the sample, where the elastic pulse causes surface 30a of the sample to move and/or otherwise change in characteristics that is optically detectable. The reference pulse thus travels in the forward direction from $BS_1$ directly to $BS_2$ and then to the sample 30.

The polarization state of the sequence of probe pulses are illustrated in FIG. 4B. In the forward direction proceeding towards the sample, the sequence of probe pulses is passed by beamsplitter $BS_1$ towards the long optical path towards $BS_2$, reflected by mirrors 62, 64 and rotated by half-wave plate 72. This causes the originally horizontal component of each of the probe pulse modulated in phase or frequency by modulator 56 to become the phase or frequency modulated vertical component and the vertical component originally unaffected by the modulator 56 to become the unmodulated horizontal component as shown in FIG. 4B. Polarizing beamsplitter 66 passes only the unmodulated horizontal components of the probe pulses through lens 68 to sample 30 and blocks the modulated vertical components.

The length of the long optical path between the two beamsplitters $BS_1$, $BS_2$, and mirrors 62, 64 is such that the horizontal component of each of the probe pulses reach sample 30 after the corresponding pump pulse has created an elastic pulse in sample 30 as described above. The elastic pulse may cause surface 30a of the sample to move as well as change in other optically detectable characteristics of the sample surface. These components of the probe pulses are modified by such effects of the elastic pulse upon reflection by the sample surface. By adjusting the variable optical delay 34' by means of stage 50, it is possible to direct the horizontal components of the probe pulses to sample 30 at different times after an elastic pulse has been created by means of the corresponding pump pulse.

As noted above, the elastic pulses cause surface 30a of the sample to move and/or change in other characteristics of the sample surface that are detectable optically. When so modified and reflected by sample 30, the reflected probe pulses travel back in the reverse direction through lens 68, polarizing beamsplitter 66, beamsplitters $BS_2$, $BS_1$ in the short path without reaching mirrors 62, 64 and are then reflected by mirror 74 to polarizing beamsplitter 76. Polarizing beamsplitter 76 is preferably oriented with its polarizing axis at 45° to the horizontal plane, so that it passes a component of each reflected probe pulse along its axis to detector 82 and reflects a component of each reflected probe pulse normal to its axis to detector 84.

Referring now to FIG. 4A, the horizontal component of each of the reference pulses modulated by modulator 56 proceeding towards sample 30 is reflected by sample 30. Since such component reaches the sample before the elastic pulse is created by the corresponding pump pulse, such modulated horizontal component of the reference pulses will be reflected by sample 30 as the reflected reference pulse in a manner not affected by the elastic pulse, pass through lens 68, polarizing beamsplitter 66 and partially reflected by beamsplitter $BS_2$ towards half-wave plate 72. Half-wave plate 72 causes the modulated and horizontally polarized reflected reference pulse to be rotated so that the reflected reference pulse is now polarized in the vertical direction. After reflection by mirrors 64, 62, this modulated and reflected reference pulse is partially reflected by $BS_1$ and further reflected by mirror 74 towards polarizing beamsplitter 76. Polarizing beamsplitter 76 passes a component of such reflected reference pulse along its axis to detector 82 and reflects the component perpendicular to its axis to detector 84.

From the above description, it will be noted that the above-described portions of the reflected reference pulse reaching detectors 82 and 84 travel along optical paths between polarizing beam splitter 20' and the detectors 82, 84 that are of the same length as those traveled by the above-described portions of the corresponding reflected probe pulse originating from the same laser pulse. In the case of the reflected reference pulse, the reference pulse travels first through the short path from $BS_1$ to $BS_2$ in the forward direction and its reflection returns from $BS_2$ via mirrors 64 and 62 in the long path to $BS_1$ in the reverse direction. In the case of the reflected probe pulse, the probe pulse travels first from $BS_1$ and reflected by mirror 62, 64 in the long path to $BS_2$ in the forward direction and its reflection returns from $BS_2$ to $BS_1$ along the short path in the reverse direction. Therefore, the above-described portions of the reflected reference pulse reach detector 82 at substantially the same time as the corresponding portions of the above-described probe pulse and would interfere at such detector. In the same vein, the portions of the reflected reference pulse described above reaching detector 84 would arrive at such detector at substantially the same time as the portions of the corresponding reflected probe pulse, and would interfere with such portions at the detector.

In reference to FIG. 2, the polarizing beamsplitter 76 reflects a portion of the interfering pulses and transmits the remainder. Beamsplitter 76 also introduces a 180° phase shift between the reflected and transmitted portions of the interfering pulses. By subtracting the outputs of the two detectors 82, 84 in mixer 86, a differential signal is obtained, where such differential signal is much less dependent on the reflectivity of the sample surface and much more sensitive to the change in phase caused by the movement of the surface. By introducing a phase or frequency shift by means of modulator 56, the differential signal will now contain components at the operating frequency of the modulator 56 and its harmonics. In one embodiment, modulator 56 may be operated at around 50 kHz. By operating at such high frequency, the effects of low frequency noise caused by the environment and mechanical vibrations is much reduced so that the system of FIG. 2 is advantageous over homodyne systems.

The differential signal from mixer 86 is applied to lock-in amplifier 42. Modulator 56 is driven at a predetermined operating frequency by driver 62. Drivers 60 and 62 supply the modulation frequencies $f_{pump}$, $f_{probe}$ of respectively the pump and probe/reference pulses to lock-in amplifier 42 which amplifies only at a selected frequency such as a mixing frequency given by the difference $f_{pump}-f_{probe}$ between the driving frequencies of drivers 60 and 62, or a frequency given by the sum or difference between any multiple of the driving frequency $f_{pump}$ of driver 60 and any multiple of the driving frequency $f_{probe}$ of driver 62. Lock-in amplifier 42 may also be used to amplify signals at different mixing frequencies and obtain the ratios of the amplified signals at different mixing frequencies for calibration and for reducing laser noise.

In reference again to FIG. 4A, in addition to the portion of each reflected reference pulse that is reflected by beamsplitter $BS_2$ along the long path as described above, $BS_2$ will also pass a portion of such reflected reference pulse directly to beamsplitter $BS_1$ along the short path and to the detectors 82, 84. However, since such portion of the reflected reference pulse travels along an optical path that is shorter than the path traveled by the above-described portion of the corresponding probe pulse, such portion of the reference pulse will arrive at the detectors before the arrival of the portion of the corresponding probe pulse and, therefore, will not interfere therewith.

In the preferred embodiment, laser 12 is a femtosecond laser and provides laser pulses each of a duration of the order of femtoseconds. These pulses therefore have extremely wide bandwidths. Hence, when the same pulse is divided into different portions, only portions originating from the same pulse will interfere and only where the different portions have traveled substantially the same optical path lengths. Portions divided from different pulses are incoherent relative to one another and do not typically interfere. Thus, by using the common path configuration of FIG. 2, only the portions of radiation divided from the same pulse and traveling the same optical path length will interfere.

As noted above, where the interfering probe and reference pulses do not travel along a common path, environmental factors may affect the two interfering pulses differently, thereby creating background noise. Where the interfering probe and reference pulses travel along the same optical path, even though they travel along the short and long paths at different times as noted above, noise caused by environmental factors is much reduced. Thus, in a common path configuration as described above, environmental disturbance affects both the reference and probe pulses in substantially the same way so that the effects of the disturbance are self-canceling in the interference.

Where the interfering reference and probe pulses travel along a common path, in order to perform heterodyne interferometry, one would need to modulate the reference and probe pulses differently. In the embodiment of FIGS. 2, 4A, 4B, this is performed by orienting the photo-elastic modulator 56 so that it modulates electric field of radiation only in a specific direction so that even though the reference and probe pulses travel along the same path, it is possible to modulate the pulses so that when the pair of pulses interfere at the detector, only one of the two pulses has been modulated by modulator 56. Obviously, it will possible to add another modulator for modulating the vertical component at a frequency that is different from modulator 56 so that one of the pair of pulses is modulated at such frequency whereas the other of the pair of pulses is modulated at the frequency of modulator 56. In such event, the differential signal is given by the difference between the two modulation frequencies. Still other modulation schemes are possible. Such and other variations are within the scope of the invention.

The above-described heterodyne interferometry scheme has high sensitivity compared to intensity modulation. Since phase modulation depth of many materials is generally larger than intensity modulation depth, the useful part of the probe beam power is increased, leading to high sensitivity. Alternatively, to maintain the same sensitivity as that in the homodyne detection, the probe beam power may be reduced. In the phase modulation scheme as that described above, it is possible to obtain signals related to the first, second or higher harmonics of phase modulation frequency. These signals may be used for calibration or to reduce noise.

FIGS. 5A–5D illustrate the timing and changes to corresponding pulses in the pump, reference and probe beams in the embodiment of FIGS. 2, 4A and 4B. FIG. 5A illustrates the pump pulse and the pulse from which the pair of corresponding probe and reference pulses is derived. As shown in FIG. 5A, the pulse from which the pair of probe and reference pulses is derived is polarized with a component $A(t)\cos\omega_0 t$ in the horizontal plane and no vertical component, upon passing the polarizing beamsplitter 20'. The point in time when the pulses emerge from polarizing beamsplitter 20' is indicated as t in FIG. 5A. Since the horizontal plane in the embodiment of FIG. 2 is also the plane of incidence of the beams at sample 30, the horizontal component is thus the P-polarized component and the vertical component is the S-polarized component. Therefore, the pulse from which the pair of probe and reference pulses is derived, upon emerging from the polarizing beamsplitter 20', has only a P-polarized component and is given by:

$$\vec{E} = \begin{bmatrix} A(t)\cos\omega_0 t \\ 0 \end{bmatrix} \quad (1)$$

where $\omega_0$ is the angular frequency of radiation and $A(t)$ is the amplitude of the radiation pulse. Equation 1 above indicates the state of the probe and reference pulses before splitting upon emerging from polarizing beamsplitter (PBS) 20' at time t in the manner described above, the reference pulse passes from $BS_1$ directly to $BS_2$ and reaches the sample surface; the reference pulse on the sample just before reflection by the sample is given by:

$$\vec{E}_R = \begin{bmatrix} t_R A(t')\cos\left(\omega_0 t' + \frac{\pi}{2}\cos\omega_C t'\right) \\ 0 \end{bmatrix}, \quad t' = t + (\tau_1 + \tau_R) \quad (2)$$

where $t_R$ is the transmission coefficient of the reference path, $\omega_C$ is the angular frequency of PEM phase modulation (carrier frequency), $\tau_P$ (see FIG. 5B) represents the time required for radiation to travel from the PBS 20' to the sample, along the pump path, $\tau_1$ represents the time for radiation to travel from the PBS 20' to $BS_1$ and $\tau_R$ represents the time for radiation to travel from $BS_1$ to the sample, along the short path.

In the manner described above, the probe pulse travels along the long path from $BS_1$ to mirror 62, 64 and to $BS_2$; when such pulse reaches the sample surface, it is P-polarized and is given by:

$$\vec{E}_S = \begin{bmatrix} t_S A(t'')\cos\omega_0 t'' \\ 0 \end{bmatrix}, \quad t'' = t + (\tau_1 + \tau_S) \quad (3)$$

where $t_S$ is the transmission coefficient of the probe signal path and $\tau_S$ represents the time for radiation to travel from $BS_1$ to the sample, along the long path.

The reference pulse is reflected by the sample surface and is given by:

$$\vec{E}_R = \begin{bmatrix} r_0 t_R A(t')\cos\left(\omega_0 t' + \frac{\pi}{2}\cos\omega_C t'\right) \\ 0 \end{bmatrix}, \quad t' = t + (\tau_1 + \tau_R) \quad (4)$$

where $r_0$ is the reflection coefficient of the sample surface, without photo-acoustic induced reflection coefficient change.

The probe pulse is reflected by the sample surface and modified by movement of the sample surface and other optically detectable phenomenon caused by the elastic pulse; the reflected probe pulse being given by:

$$\vec{E}_S = \begin{bmatrix} t_S r(t'')A(t'')\cos\left(\omega_0 t'' + \frac{4\pi}{\lambda_0}u\cos\omega_S t''\right) \\ 0 \end{bmatrix}, \quad t'' = t + (\tau_1 + \tau_S) \quad (5)$$

where $r(t'')$ is the reflection coefficient of the sample surface, including photo-acoustic induced reflection coefficient change; $u$ is the photo-acoustic induced surface displacement and $\omega_S$ is the angular frequency of photo-acoustic signals.

The reflected reference pulse travels along the long path from $BS_2$ to mirrors 64, 62 to $BS_1$ and appears at beamsplitter 76; the reference pulse reaching beamsplitter 76 is S-polarized and is given by:

$$\vec{E}_R = \begin{bmatrix} 0 \\ r_0 t_R A(t''')\cos\omega_0 t''' + \frac{\pi}{2}\cos\omega_C t''' \end{bmatrix}, \quad (6)$$

$$t''' = t - (\tau_1 + \tau_2 + \tau_R + \tau_S)$$

where $\tau_2$ represents the time for radiation to travel from $BS_1$ to the PBS 76 at 45°.

The reflected probe pulse travels in the reverse direction along the short path from $BS_2$ to $BS_1$ directly and reaches the polarizing beamsplitter 76; such reflected probe pulse is given by:

$$\vec{E}_S = \begin{bmatrix} t_S r(t''')A(t''')\cos\left(\omega_0 t''' + \frac{4\pi}{\lambda_0}u\cos\omega_S t'''\right) \\ 0 \end{bmatrix}, \quad (7)$$

$$t''' = t - (\tau_1 + \tau_2 + \tau_R + \tau_S)$$

FIG. 6 is a graphical plot obtained from an experiment of the phase shift detected between the reference and probe pulses as a function of time as detected from a layer of 96 nm and a layer of 180 nm thick titanium film on a thick substrate of silicon. By changing the varying delay 34', it is possible to detect the position of surface 30a at different times to yield the phase shift curve between the reference and probe pulses shown in FIG. 6. Since the silicon substrate is thick, the reflection from the bottom of the substrate may be ignored. As shown in FIG. 6, for the 96 nm layer, the pump beam causes an acoustic pulse to be generated with high amplitude at about 0 picoseconds from an arbitrary time zero. This acoustic pulse propagates downwards through the titanium film and is reflected by the interface between the film and the silicon substrate underneath. When the reflection reaches the sample surface 30a, it causes the surface to move and is detected as the first echo at about 28 picoseconds from zero. The first echo propagates downwards and is again reflected by the titanium/silicon interface and the echo propagates upwards to reach the sample surface as the second echo and detected at about 60 picoseconds from zero. Thus, the time that it takes the acoustic pulse to travel from the first echo at 28 picoseconds from the air/titanium interface towards the titanium/silicon interface and back towards the titanium/air interface as the second echo took (60–28) picoseconds. If the speed of sound in titanium is known, then the thickness of the titanium film is given by such speed times half of the time interval between the first and second echos as shown in FIG. 6. As noted above, the change in height or elevation of the sample surface 30a is proportional to the phase shift between the reference and probe pulses detected by detector 96. Since the primary interest is to detect the timing interval between the first and second echos (or between the time the pump pulse reach the surface 30a and the first echo), it would be adequate to simply derive the time period between the time of the pump pulse reaching the surface and the first echo or that between the first and second echos from a plot of the phase shift without actually calculating the height change of the surface. As also shown in FIG. 6, for the 180 nm layer, the first echo occurs at about 58 picoseconds, and the same calculation may be made by obtaining the time interval between the pump pulse reaching the surface at time 0 and the first echo (58 picoseconds).

Lock-in amplifier 42 and motor controller 44 supplies outputs to data acquisition and personal computer 18 which performs calculations to derive a graphical plot such as that shown in FIG. 6. The echos of acoustic-pulses may therefore be discerned from the graphical plot and film thickness obtained thereby.

FIG. 7 is a schematic view of a second embodiment 10B of the system of FIG. 1. Embodiment 10B of FIG. 7 differs from embodiment 10A of FIG. 2 in that a half-wave plate 54' is used instead of a quarter-wave plate as in system 10A of FIG. 2. The relative orientation of the half-wave plate 54' relative to the polarization plane of the laser 12 and modulator 56 is illustrated in FIG. 8. As shown in FIG. 8, the axis of the half-wave plate 54' is oriented preferably at 22.5° to the horizontal plane or plane of incidence, so that the beam emerging from plate 54' and reaching modulator 56 is a beam that is linearly polarized instead of circularly polarized as in FIG. 2, where the plane of polarization of such beam is at 45° to the horizontal plane. The above-described analysis for the embodiment of FIGS. 2, 4A and 4B applies also to embodiment 10B of FIG. 7 except that the signal at the mixing frequency $f_{probe}-f_{pump}$ of embodiment 10B would correspond to the signal at the mixing frequency $2f_{probe}-f_{pump}$ in the embodiment of FIGS. 2, 4A and 4B.

In the embodiments of FIGS. 2, 4A and 4B and of FIGS. 7 and 8, the vertical and horizontal (S- and P-polarized) components have substantially equal amplitudes. This is preferable since this would yield the maximum signal at the detectors 82, 84. This is accomplished by orienting axis of plate 54 at 45° to the horizontal plane in embodiment 10A, and axis of plate 54' at 22.5° to the horizontal plane in embodiment 10A. It will be udnerstood that this is not required and other orientations are possible and are within the scope of the invention.

Instead of using a photo-elastic modulator 56 in combination with the quarter-wave plate or a half-wave plate as in prior embodiments, it is also possible to omit the quarter-wave or half-wave plate and use a photo-elastic modulator oriented with its modulation axis at an angle to the horizontal plane or plane of incidence as illustrated in FIGS. 9 and 10. Thus, in the embodiment 10C of FIGS. 9 and 10, modulator 56' is oriented with its modulation axis preferably at 45° to the horizontal plane or plane of incidence, so that the component of the radiation along the modulation axis will be modulated whereas the component perpendicular to such axis will not. Substantially the same analysis applicable to the second embodiment of FIGS. 7 and 8 are applicable here to embodiment 10C as well. Aside from such difference the third embodiment of FIG. 9 and 10 operates in substantially the same way as the prior embodiments.

FIG. 11 illustrates a heterodyne/common-path interferometer 10D which is yet another embodiment of the system of FIG. 1. System 10D differs from system 10C of FIGS. 9 and 10 only in the location of the photo-elastic modulator 56' in the optical arrangement. Instead of being placed between the polarizing beamsplitter 20' and $BS_1$, the photo-elastic modulator 56' is placed in the long path between $BS_1$ and $BS_2$ as shown in FIG. 11. Modulator 56' may be oriented with its modulation axis preferably at 45° to the horizontal plane as illustrated in FIG. 10 in the embodiment of FIGS. 9 and 10.

FIG. 12 is a schematic diagram of a heterodyne/common-path interferometer 10E, which is yet another embodiment of the system of FIG. 1. System 10E differs from system 10D of FIG. 11 only in the location of the photo-elastic modulator 56'''. Instead of placing the modulator in the long path between beamsplitter $BS_1$ and $BS_2$ that includes the two mirrors, modulator 56''' is now placed in the short path, that is the path that directly connects $BS_1$ and $BS_2$. Again, modulator 56''' is preferably oriented with its modulation axis preferably at 45° to the horizontal plane or plane of incidence. System 10E functions in substantially the same way as the embodiments described above.

FIGS. 13 and 14 are schematic diagrams of further embodiments 10F, 10G of system 10 of FIG. 1. System 10F is substantially the same as the embodiment of FIGS. 2, 4A and 4B, except that an electro-optic modulator 156 is used instead of a photo-elastic modulator. Similarly, system 10G of FIG. 14 is similar to the embodiment of FIGS. 7 and 8 except that an electro-optic modulator 156 is used instead of a photo-elastic modulator. Aside from such differences, systems 10F, 10G function and operate in substantially the same manner as embodiments 10A, 10B described above.

FIG. 15 is a schematic diagram of a system 10H which is yet another embodiment of the system 10 of FIG. 1. As before, the sequence of pulses from laser 12 is divided by polarizing beamsplitter 20' into a sequence of pump pulses and other pulses from which pairs of reference and probe pulses are derived. After being modulated by acoustic opto-modulator 24 and focused by lens L, the sequence of pump pulses is supplied to sample 30 through an optical fiber 102 having a varying delay loop 34'' therein driven by a driver 44 for varying the delay. The sequence of pulses passed by polarizing beamsplitter 20' is fed to a 3-dB coupler 104 through a lens L and an optical fiber. Coupler 104 is coupled to another three-dB coupler 106 through a pair of optical fibers 108 and 110, where optical fiber 110 is much longer than optical fiber 108 as shown in FIG. 15. The difference in length between the two fibers 110 and 108 therefore serves as a fixed delay loop. A phase modulator 112 is placed adjacent to fiber 110 for modulating the phase of radiation signals in the fiber. Thus, by adjusting varying delay 34'', a portion of the pulse passed by polarizing beamsplitter 20' traveling along the short path in fiber 108 would reach the sample 30 before the arrival of the pump pulse through fiber 102 and therefore serves as the reference pulse. The reflected reference pulse travels along the long fiber 110 and is modulated by phase modulator 112 and arrives at the detector 82'. The other portion of radiation passed by polarizing beamsplitter 20' travels along the long path 110 and is modulated by phase modulator 112 before reaching the sample 30 after an elastic pulse has been created in the sample by the corresponding pump pulse supplied through fiber 102. The probe pulse is modified by the movement and other optically detectable characteristics of the sample surface so that the modified and reflected probe pulse returns through the short path in fiber 108 to detector 82'. Thus, the reference pulse is modulated in phase by the phase modulator 112 in its return path in the reverse direction of travel whereas the probe pulse is modulated by the phase modulator in its forward travel direction. The pair of corresponding reference and probe pulses are therefore modulated at different times by the phase modulator 112 so that there is a net time-dependent phase difference between them. Therefore, when the above-described reflected reference and probe pulses arrive at detector 82' at about the same time, they would interfere as before from which film thickness and other useful information may be derived by means of data acquisition and computer 18. While the wide bandwidth and short femtosecond pulses may disperse in the optical fibers in the embodiment of FIG. 15, such dispersion can be accounted for.

FIG. 16 is a cross-sectional view of a sample 30 comprising a layer 30' of metal formed by a conventional method such as deposition over a substrate S to illustrate the invention. Thus, typically the metal layer 30' may be deposited on one or more layers over the substrate S, such as a dielectric layer 30'' (e.g. silicon dioxide) on the silicon substrate, and there may be yet possible additional layers such as layer 30''' over the metal layer 30'. As shown in FIG. 16, sample 30 may comprise a substrate with layers 30', 30'', 30''' and other possible layers thereon; although for simplicity only layers 30', 30'', 30''' are shown in FIG. 16. Layer 30' may be formed by deposition of a metal material, such as aluminum or copper, on layer 30'' over the substrate S. The thickness of layer 30' and of other layers in sample 30 may be determined by the techniques described above.

While in the embodiments described above, the reference and probe pulses are modified by the sample by being reflected by the sample surface, it will be understood that it is also possible to modify the reference and probe pulses by passing such pulses through the sample and returning the portions of the pulses that have passed through the sample to interfere at the detector instead. In the embodiments described above, the reference and probe pulses are directed towards the same or two substantially overlapping spots on the sample surface. However, even if the reference pulses and corresponding probe pulses are directed at different areas of the sample, such as by passing the pulses through birefringent crystal, such modified system will operate in essentially the same way as those described above, and afforded with the same advantages. This is the case when each reference pulse and its corresponding probe pulse travel substantially along the same common path so that noise caused by environmental factors on the two pulses does not materially interfere with the accuracy of measurement. Such and other variations are within the scope of the invention.

The thickness of films or layers encountered in semiconductors can range from several hundred microns to tens of Angstroms. As semiconductor device continue to shrink, the thicknesses of different layers of films that are to be measured in semiconductors are continually reduced. In order to provide adequate resolution for detecting such thin films and layers, the pulses employed are preferably of short durations, such as in the range of femtoseconds. At the present state of the art, probe and reference pulses having durations of less than 10 picoseconds may be adequate for some film thickness measurements, while for other measurements, probe and reference pulses having durations less than a picosecond may be desirable.

The above is true not only for the heterodyne techniques of detection in the above-described embodiments but also in a homodyne detection system, such as that shown in FIG. 17. The embodiment 10G of FIG. 17 differs from the embodiment 10A of FIG. 2 only in that the photo-elastic modulator 56 is replaced by an acousto-optic modulator 56', which modulates the intensity instead of frequency or phase (in the case of PEM 56) of the pulses from which the probe and reference pulses are derived. Thus, embodiment 10G of FIG. 17 is essentially the same as FIG. 2 of parent application Ser. No. 09/028,417 filed on Feb. 24, 1998. The parent application is incorporated herein by reference in its entirety.

In the present application, the pulses from laser 12 are modulated in phase or frequency by modulator 56 in FIG. 2, or in intensity by acousto-optic modulator 56' in FIG. 17. In both cases, such pulses have short durations as indicated above and provides for adequate resolution for measuring thin films of submicron thicknesses or even film thicknesses of the order of tens of Angstroms.

While the invention has been described above by reference to various embodiments, it will be understood that changes and modifications may be made without departing from the scope of the invention, which is to be defined only by the appended claims and their equivalents. All of the reference referred to above are incorporated herein in their entirety by reference.

What is claimed is:

1. A system for non-destructively measuring properties of a sample, comprising:
    a first optical source supplying a pump pulse of radiation to a first surface area of the sample to non-destructively generate an elastic pulse in the sample, said elastic pulse influencing said first surface area; and
    an interferometer providing an output, said interferometer including:
        a second optical source providing a pair of a probe pulse and a reference pulse of radiation that are substantially in phase with each other;
        a detector;
        optics directing the probe pulse to said first surface area when it is influenced by the elastic pulse and the reference pulse to a second surface area of the sample so that the pair of pulses are modified by the sample, so that the modified pulses interfere at the detector and so that the probe pulse together with the modified probe pulse substantially share a common optical path with the reference pulse together with the modified reference pulse between the second optical source and the detector; and
        a first modulator in the common optical path modulating phase or frequency of at least one of the pair of pulses before or after modification by the sample.

2. The system of claim 1, wherein said second optical source provides femtosecond pulses.

3. The system of claim 1, said modulator modulating an electric field of said one of the pair of pulses substantially in only one direction.

4. The system of claim 3, said modulator comprising a photo-elastic or electro-optic modulator.

5. The system of claim 4, said modulator further comprising a quarter or halfwave plate in the common optical path between the second optical source and the photo-elastic or electro-optic modulator, said second optical source providing radiation polarized along an axis, said photo-elastic or electro-optic modulator oriented to modulate the electric field of one of the pair of pulses substantially only along the axis or in a direction substantially normal to the axis.

6. The system of claim 4, said second optical source providing radiation polarized along an axis, said photo-elastic or electro-optic modulator oriented to modulate the electric field of one of the pair of pulses substantially only along a direction at an angle to the axis.

7. The system of claim 1, wherein said common path includes one or more optical fibers and one or more optical couplers.

8. The system of claim 1, wherein said optics directs the probe pulse to said first surface area when it is influenced by the elastic pulse and the reference pulse to a second surface area of the sample so that the pair of pulses are reflected by the sample and so that the reflected pulses interfere at the detector.

9. The system of claim 1, wherein said first and second areas substantially overlap.

10. The system of claim 1, said sample having at least one interface under the surface, said system further comprising a variable optical delay altering a time relationship between the pump pulse and the probe pulse in order to sense changes of the sample surface caused by said elastic pulse.

11. The system of claim 10, wherein the system senses changes in elevation of the sample surface.

12. The system of claim 10, further comprising a processing circuit deriving a distance from the at least one interface to the sample surface from said changes of the sample surface caused by said elastic pulse.

13. The system of claim 1, said first optical source supplying a sequence of said pump pulses at a first frequency, said second optical source providing a sequence of pairs of said probe and reference pulses to the sample, each pair corresponding to each of at least some of the pump pulses, wherein the modified reference and probe pulses of each pair interfere at the detector.

14. The system of claim 13, further comprising a second modulator modulating the sequence of pump pulses so that the pump pulses are supplied in intermittent bursts at a second frequency before the pump pulses reach the sample.

15. The system of claim 14, said first modulator modulating the at least one of each pair of pulses in the sequence of pairs of pulses at a third frequency before the pairs of pulses reach the first and second surface areas.

16. The system of claim 15, further comprising a circuit detecting the interferometer output at a frequency related to the second and third frequencies.

17. The system of claim 16, said circuit detecting the interferometer output at a frequency substantially equal to a difference frequency given by the difference between the second and third frequencies, or the difference between a multiple of the second frequency and a multiple of the third frequency.

18. The system of claim 16, said circuit including a lock-in amplifier.

19. The system of claim 14, said second modulator including an acousto-optic modulator.

20. The system of claim 1, said second optical source including:
a first beam splitter splitting an input pulse of radiation into the probe pulse and the reference pulse;
a second beam splitter; and
a first and a second optical path between the two beamsplitters, the second optical path having a path length longer than that of the first optical path, directions of propagation from the first beam splitter toward the second beam splitter along the two optical paths being the forward directions and the directions opposite thereto the reverse directions;
the first beam splitter being such that the reference and probe pulses propagate along the first and second optical paths respectively in the forward directions so that the reference pulse reaches the sample before the probe pulse.

21. The system of claim 20, wherein the second beam splitter causes modified reference and probe pulses to travel along the second and first optical paths respectively in the reverse directions, so that the total optical path length traveled by the reference pulse and its modification by the sample is substantially the same as the total optical path length traveled by the probe pulses and its modification by the sample.

22. The system of claim 20, wherein the first beam splitter reflects the reference pulse towards the first optical path in a forward direction and reflects the modified reference pulse from the second optical path in a reverse direction.

23. The system of claim 20, wherein the first beam splitter passes the probe pulse towards the second optical path in a forward direction, and passes the modified probe pulse from the first optical path in a reverse direction.

24. The system of claim 20, wherein the second beam splitter passes the reference pulse from the first optical path in a forward direction and reflects the modified reference pulse towards the second optical path in a reverse direction.

25. The system of claim 20, wherein the second beam splitter reflects the probe pulse from the second optical path in a forward direction, and passes the modified probe pulse to the first optical path in a reverse direction.

26. The system of claim 20, wherein the second optical path includes a half-wave plate.

27. The system of claim 20, wherein the first modulator is in the first or second optical path.

28. The system of claim 27, said second optical source providing radiation polarized along an axis, said modulator oriented to modulate the electric field of one of the pair of pulses substantially only along a direction at an angle to the axis.

29. The system of claim 1, wherein said first optical source supplies the pump pulse along a path towards the sample that is spatially separated from a path of the pair of pulses towards the sample.

30. The system of claim 1, wherein optics directs the probe pulse to the first surface area when it is moved by the elastic pulse.

31. A system for non-destructively measuring properties of a sample, comprising:
means for supplying a pump pulse of radiation to a first surface area of the sample to non-destructively generate an elastic pulse in the sample, said elastic pulse influencing said first surface area; and
an interferometer providing an output, said interferometer including:
means for providing a pair of a probe pulse and a reference pulse of radiation that are substantially in phase with each other;
a detector;
means for directing the probe pulse to said first surface area when it is influenced by the elastic pulse and the reference pulse to a second surface area of the sample so that the pair of pulses are modified by the sample, so that the modified pulses interfere at the detector and so that the probe pulse together with the modified probe pulse substantially share a common optical path with the reference pulse together with the modified reference pulse between the second optical source and the detector; and means in the common optical path for modulating phase or frequency of one of the pair of pulses before or after modification by the sample.

32. The system of claim 31, wherein said directing means directs the probe pulse to the first surface area when it is moved by the elastic pulse.

33. A method for non-destructively measuring properties of a sample, comprising:

supplying a pump pulse of radiation to a first surface area of the sample to non-destructively generate an elastic pulse in the sample, said elastic pulse influencing said first surface area; and providing a pair of a probe pulse and a reference pulse of radiation that are substantially in phase with each other;

directing the probe pulse to said first surface area when it is influenced by the elastic pulse and the reference pulse to a second surface area of the sample so that the pair of pulses are modified by the sample, so that the modified pulses interfere at a detector to provide an output, and so that the probe pulse together with the modified probe pulse substantially share a common optical path with the reference pulse together with the modified reference pulse between the second optical source and the detector; and modulating phase or frequency of one of the pair of pulses before or after modification by the sample.

34. The method of claim 33, wherein said providing provides femtosecond pulses.

35. The method of claim 33, wherein said modulating modulates an electric field of said one of the pair of pulses substantially in only one direction.

36. The method of claim 33, said modulating being performed by means of a photo-elastic or electro-optic modulator.

37. The method of claim 36, wherein said providing provides radiation polarized along an axis, said method further comprising orienting said photo-elastic or electro-optic modulator to modulate the electric field of one of the pair of pulses substantially only along a direction at an angle to the axis.

38. The method of claim 33, wherein said directing directs the probe pulse to said first surface area when it is influenced by the elastic pulse and the reference pulse to a second surface area of the sample so that the pair of pulses are reflected by the sample and so that the reflected pulses interfere at the detector.

39. The method of claim 33, wherein said first and second areas substantially overlap.

40. The method of claim 33, said sample having at least one interface under the surface, said method further comprising altering a time relationship between the pump pulse and the probe pulse in order to sense changes of the sample surface caused by said elastic pulse.

41. The method of claim 40, wherein said altering alters an optical length of an optical delay path.

42. The method of claim 40, wherein the method senses changes in elevation of the sample surface.

43. The method of claim 40, further comprising deriving a distance from the at least one interface to the sample surface from said changes of the sample surface caused by said elastic pulse.

44. The method of claim 33, wherein said supplying supplies a sequence of said pump pulses at a first frequency, and said providing provides a sequence of pairs of said probe and reference pulses to the sample, each pair corresponding to each of at least some of the pump pulses, wherein the modified reference and probe pulses of each pair interfere at the detector.

45. The method of claim 44, further comprising modulating the sequence of pump pulses so that the pump pulses are supplied in intermittent bursts at a second frequency before the pump pulses reach the sample.

46. The method of claim 45, wherein one of each pair of pulses in the sequence of pairs of pulses is modulated at a third frequency before the pairs of pulses reach the first and second surface areas.

47. The method of claim 46, further comprising detecting the output at a frequency related to the second and third frequencies.

48. The method of claim 47, wherein said detecting detects the output at a frequency substantially equal to a difference frequency given by the difference between the second and third frequencies, or the difference between a multiple of the second frequency and a multiple of the third frequency.

49. The method of claim 33, wherein said supplying supplies the pump pulse along a path towards the sample that is spatially separated from a path of the pair of pulses towards the sample.

50. The method of claim 33, wherein said directing directs the probe pulse to the first surface area when it is moved by the elastic pulse.

51. A method for non-destructively measuring properties of a sample, comprising:

forming a layer of material on a substrate to make a sample;

supplying a pump pulse of radiation to a first surface area of the sample to non-destructively generate an elastic pulse in the sample, said elastic pulse influencing said first surface area; and providing a pair of a probe pulse and a reference pulse of radiation that are substantially in phase with each other;

directing the probe pulse to said first surface area when it is influenced by the elastic pulse and the reference pulse to a second surface area of the sample so that the pair of pulses are modified by the sample, so that the modified pulses interfere at a detector to provide an output, and so that the probe pulse together with the modified probe pulse substantially share a common optical path with the reference pulse together with the modified reference pulse between the second optical source and the detector; and modulating phase or frequency of one of the pair of pulses before or after modification by the sample.

52. A system for non-destructively measuring properties of a sample, comprising:

a first optical source supplying a pump pulse of radiation to a first surface area of the sample to non-destructively generate an elastic pulse in the sample, said elastic pulse influencing said first surface area; and an interferometer providing an output, said interferometer including:

a second optical source providing a pair of a probe pulse and a reference pulse of radiation that are substantially in phase with each other;

a detector;

optics directing the probe pulse to said first surface area when it is influenced by the elastic pulse and the reference pulse to a second surface area of the sample so that the pair of pulses are modified by the sample, and so that the modified pulses interfere at the detector; and a modulator in the common optical path modulating phase or frequency of at least one of the pair of pulses before or after modification by the sample.

53. A method for non-destructively measuring properties of a sample, comprising:

supplying a pump pulse of radiation to a first surface area of the sample to non-destructively generate an elastic pulse in the sample, said elastic pulse influencing said first surface area; and providing a pair of a probe pulse and a reference pulse of radiation that are substantially in phase with each other;

directing the probe pulse to said first surface area when it is influenced by the elastic pulse and the reference pulse to a second surface area of the sample so that the pair of pulses are modified by the sample and so that the modified pulses interfere at a detector to provide an output; and modulating phase or frequency of one of the pair of pulses before or after modification by the sample.

54. A method for non-destructively measuring properties of a sample, comprising:

forming a layer of material on a substrate to make a sample;

supplying a pump pulse of radiation to a first surface area of the sample to non-destructively generate an elastic pulse in the sample, said elastic pulse influencing said first surface area; and providing a pair of a probe pulse and a reference pulse of radiation that are substantially in phase with each other;

directing the probe pulse to said first surface area when it is influenced by the elastic pulse and the reference pulse to a second surface area of the sample so that the pair of pulses are modified by the sample and so that the modified pulses interfere at a detector to provide an output; and modulating phase or frequency of one of the pair of pulses before or after modification by the sample.

55. A system for non-destructively measuring properties of a sample, comprising:

a first source supplying a pump pulse of radiation to a first surface area of the sample to non-destructively generate an elastic pulse in the sample, said elastic pulse causing said surface area to move; and an interferometer providing an output, said interferometer including:

a detector;

a second source providing a pair of a probe pulse and a reference pulse of radiation and for directing the probe pulse to said first surface area when it is moved by the elastic pulse and the reference pulse to a second surface area so that the pair is modified by the sample, wherein said pair of pulses have durations of less than about 10 picoseconds; and optics directing the modified pair of pulses to the detector so that the modified pair interferes at the detector to cause the detector to provide said output.

56. The system of claim 55, further comprising a modulator modulating the pair of probe and reference pulses or a pulse from which the pair of pulses is derived.

57. The system of claim 56, said modulator modulating the phase, frequency or intensity of the pair of pulses.

58. The system of claim 55, said optics further comprising a polarizing beamsplitter that reflects a first portion and transmits a second portion of the interfering pair of pulses and introduces a phase difference between the two portions.

59. The system of claim 58, said system including a first detector detecting the first portion to provide an output, a second detector detecting the second portion to provide an output, and a device subtracting the two detector outputs to obtain a differential signal.

60. A method for non-destructively measuring properties of a sample, comprising:

supplying a pump pulse of radiation to a first surface area of the sample to non-destructively generate an elastic pulse in the sample, said elastic pulse causing said surface area to move;

providing a pair of a probe pulse and a reference pulse of radiation, wherein said pair of pulses have durations of less than about 10 picoseconds;

directing the probe pulse to said first surface area when it is moved by the elastic pulse and the reference pulse to a second surface area so that the pair of pulses are modified by the sample; and interfering the pair of modified pulses to provide an output.

61. The system of claim 58, further comprising modulating the pair of probe and reference pulses or a pulse from which the pair of pulses is derived.

62. The system of claim 59, wherein said modulating modulates the phase, frequency or intensity of the pair of pulses.

63. The method of claim 60, wherein said interfering includes sending the pair of modified pulses to a polarizing beamsplitter that reflects a first portion and transmits a second portion of the interfering pair of pulses and introduces a phase shift there between.

64. The method of claim 63, said interfering including detecting the phase shifted two portions to provide two output signals and subtracting the two output signals.

* * * * *